United States Patent [19]

Macevicz

[11] Patent Number: 5,002,867

[45] Date of Patent: Mar. 26, 1991

[54] NUCLEIC ACID SEQUENCE DETERMINATION BY MULTIPLE MIXED OLIGONUCLEOTIDE PROBES

[76] Inventor: Stephen C. Macevicz, 21890 Rucker Dr., Cupertino, Calif. 95014

[21] Appl. No.: 261,702

[22] Filed: Oct. 24, 1988

Related U.S. Application Data

[63] Continuation-in-part of Ser. No. 186,053, Apr. 25, 1988, abandoned.

[51] Int. Cl.$^5$ .................. C12Q 1/68; C07H 15/12; C12N 15/00; G01N 33/566
[52] U.S. Cl. .................................. 435/6; 435/810; 536/27; 935/77; 935/78; 436/501; 436/808
[58] Field of Search ................. 435/6, 810; 536/27; 935/77, 78; 436/501, 808

[56] References Cited

U.S. PATENT DOCUMENTS 4,865,968  9/1989  Orgel et al. .................... 435/6

*Primary Examiner*—Amelia Burgess Yarbrough
*Assistant Examiner*—Mindy B. Fleisher

[57] ABSTRACT

A method is provided for sequencing nucleic acids without the need to separate similarly sized DNAs or RNAs by gel electrophoresis. The method relies on the separate hybridization of multiple mixed oligonucleotide probes to a target sequence. The mixed oligonucleotide probes comprise sequences of fixed and non-fixed bases corresponding to every possible permutation of fixed and non-fixed bases less than or equal to the length of the probes. For each probe, the hybridizations provide the number of times the probe's particular sequence of fixed bases appears in the target sequence. The target sequence is then mathematically reconstructed from this data and a knowledge of the probe sequences.

23 Claims, 3 Drawing Sheets

TARGET SEQUENCE

5'-C G A A T G G A A C T A C C G T A A C C T-3'

| PROBE | Positions | PERFECT MATCHES |
|---|---|---|
| A000 | A000 at positions 3, 8, 15 | 3 |
| 0A00 | 0A00 at positions 3, 8, 15 | 3 |
| 00A0 | 00A0 at positions 3, 8, 15 | 3 |
| 000A | 000A at positions 3, 8, 15, 19 | 4 |
| AA00 | | 0 |
| A0A0 | | 0 |
| A00A | | 0 |
| 0AA0 | | 0 |
| 0A0A | | 0 |
| 00AA | | 0 |
| AAA0 | | 0 |
| AA0A | | 0 |
| A0AA | | 0 |
| 0AAA | | 0 |
| AAAA | | 0 |
| C000 | C000, C000, C000 | 3 |
| 0C00 | 0C00, 0C00 | 2 |
| 00C0 | 00C0 | 1 |
| 000C | 000C | 1 |
| CC00 | CC00 | 1 |
| C0C0 | | 0 |
| C00C | | 0 |
| 0CC0 | 0CC0 | 1 |
| 0C0C | | 0 |
| 00CC | 00CC | 1 |
| CCC0 | | 0 |
| CC0C | | 0 |
| C0CC | | 0 |
| 0CCC | | 0 |
| CCCC | | 0 |
| G000 | G000, G000 | 2 |
| 0G00 | 0G00 | 1 |
| 00G0 | 00G0 | 1 |
| 000G | 000G, 000G | 2 |
| GG00 | GG00 | 1 |
| G0G0 | | 0 |
| G00G | G00G | 1 |
| 0GG0 | 0GG0, 0GG0 | 2 |
| 0G0G | | 0 |
| 00GG | 00GG, 00GG | 2 |
| GGG0 | | 0 |
| GG0G | | 0 |
| G0GG | | 0 |
| 0GGG | | 0 |
| GGGG | | 0 |
| T000 | T000, T000, T000 | 3 |
| 0T00 | 0T00 | 1 |
| 00T0 | 00T0 | 1 |
| 000T | 000T, 000T | 2 |
| TT00 | TT00, TT00, TT00 | 3 |
| T0T0 | | 0 |
| T00T | T00T | 1 |
| 0TT0 | 0TT0, 0TT0, 0TT0 | 3 |
| 0T0T | | 0 |
| 00TT | 00TT, 00TT, 00TT | 3 |
| TTT0 | | 0 |
| TT0T | | 0 |
| T0TT | | 0 |
| 0TTT | | 0 |
| TTTT | | 0 |

FIGURE 1

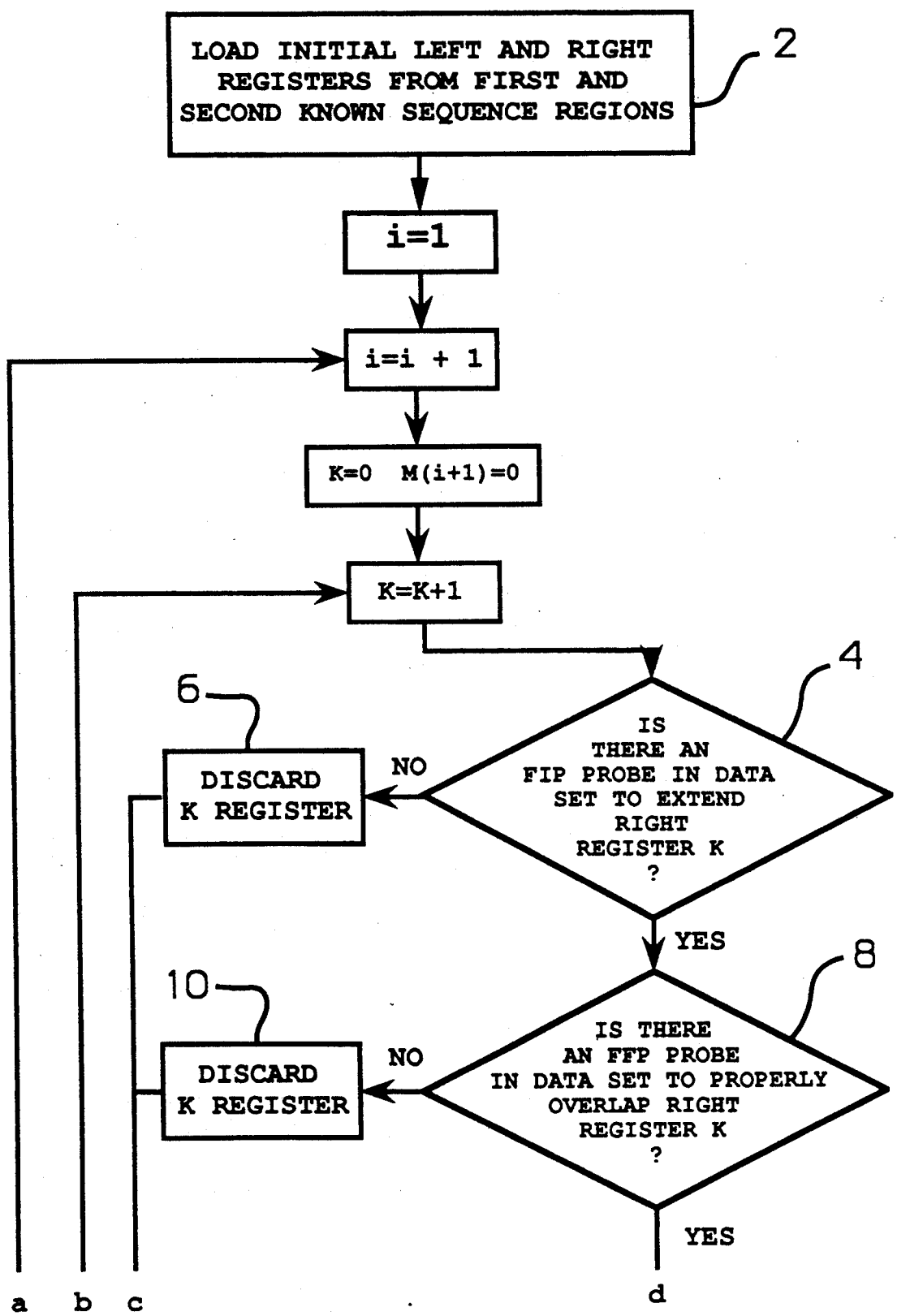
FIGURE 2 (part 1)

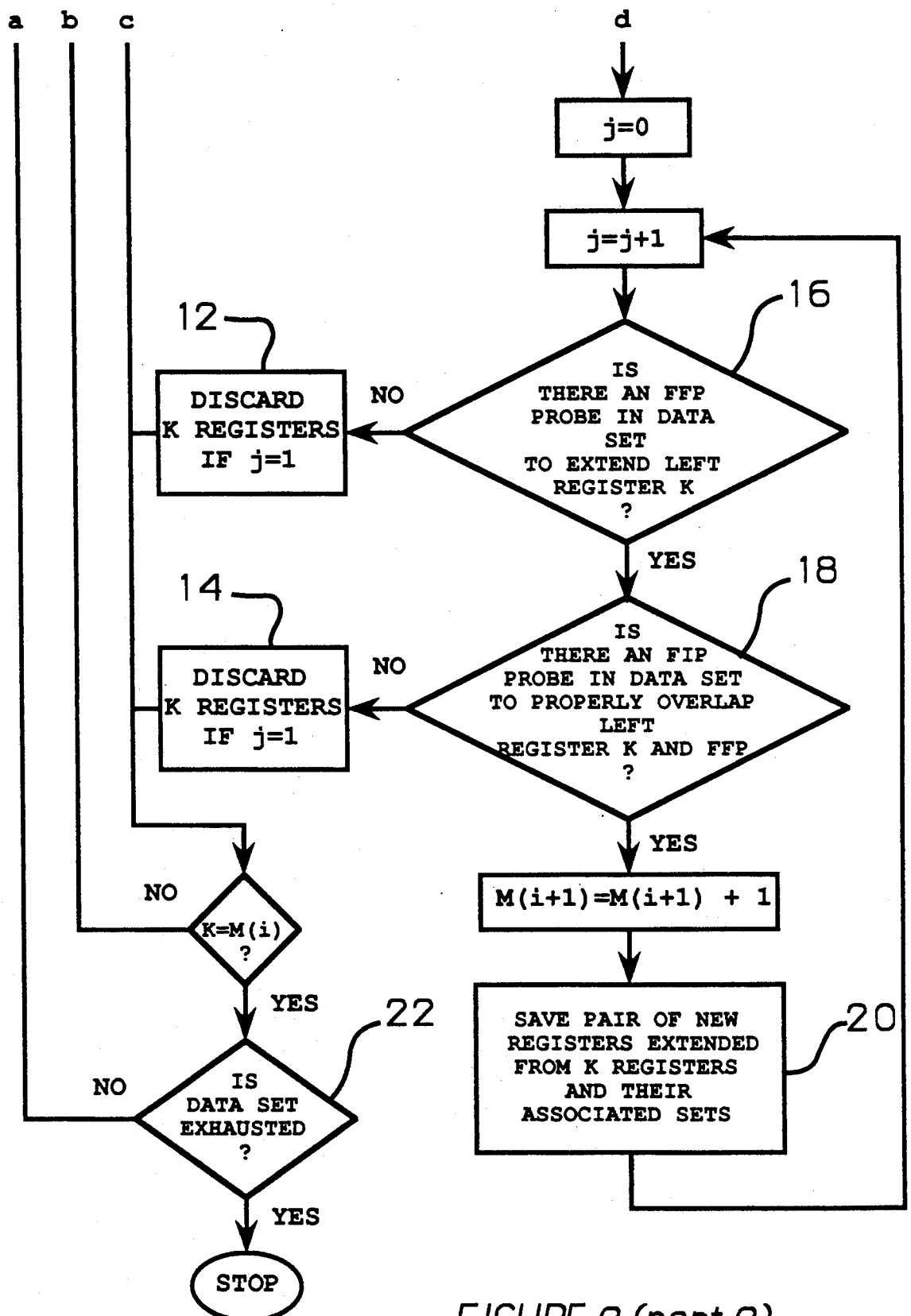
FIGURE 2 (part 2)

NUCLEIC ACID SEQUENCE DETERMINATION BY MULTIPLE MIXED OLIGONUCLEOTIDE PROBES

This is a continuation-in-part of U.S. patent application Ser. No. 186,053 filed Apr. 25, 1988, now abandoned.

FIELD OF THE INVENTION

The invention relates generally to methods for determining the sequence of a nucleic acid, and more particularly, to methods for determining the sequence of a double or single stranded deoxyribonucleic acid (DNA) by hybridization of multiple oligonucleotide probes.

BACKGROUND

The ability to determine DNA sequences is crucial for understanding the function and control of genes and for applying many of the basic techniques of molecular biology. Native DNA consists of two linear polymers, or strands of nucleotides. Each strand is a chain of nucleosides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C).

Presently there are two basic approaches to DNA sequence determination: the dideoxy chain termination method, e.g. Sanger et al, *Proc. Natl. Acad. Sci.*, Vol. 74, pgs. 5463-5467 (1977); and the chemical degradation method, e.g. Maxam et al, *Proc. Natl. Acad. Sci.*, Vol. 74, pgs. 560-564 (1977). The chain termination method has been improved in several ways, and serves as the basis for all currently available automated DNA sequencing machines, e.g. Sanger et al, *J. Mol. Biol.*, Vol. 143, pgs. 161-178 (1980); Schreier et al, *J. Mol. Biol.*, Vol. 129, pgs. 169-172 (1979); Smith et al, *Nucleic Acids Research*, Vol. 13, pgs. 2399-2412 (1985); Smith et al, *Nature*, Vol. 321, pgs. 674-679 (1987); Prober et al, *Science*, Vol. 238, pgs. 336-341 (1987), Section II, *Meth. Enzymol.*, Vol. 155, pgs. 51-334 (1987), and Church et al, *Science*, Vol 240, pgs. 185-188 (1988).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis. Unfortunately, this step severely limits the size of the DNA chain that can be sequenced at one time. Non-automated sequencing can accommodate a DNA chain of up to about 500 bases under optimal conditions, and automated sequencing can accommodate a chain of up to about 300 bases under optimal conditions, Bankier et al, *Meth. Enzymol.*, Vol. 155, pgs. 51-93 (1987); Roberts, *Science*, Vol. 238, pgs. 271-273 (1987); and Smith et al, *Biotechnology*, Vol. 5, pgs. 933-939 (1987).

This limitation represents a major bottleneck for many important medical, scientific, and industrial projects aimed at unraveling the molecular structure of large regions of plant or animal genomes, such as the project to sequence all or major portions of the human genome, Smith et al, *Biotechnology* (cited above).

In addition to DNA sequencing, nucleic acid hybridization has also been a crucial element of many techniques in molecular biology, e.g. Hames et al, eds., *Nucleic Acid Hybridization: A Practical Approach* (IRL Press, Washington, D.C., 1985). In particular, hybridization techniques have been used to select rare cDNA or genomic clones from large libraries by way of mixed oligonucleotide probes, e.g. Wallace et al, *Nucleic Acids Research*, Vol. 6, pgs. 3543-3557 (1979), *Proc. Natl. Acad. Sci.*, Vol. 80, pgs. 5842-5846 (1983). Nucleic acid hybridization has also been used to determine the degree of homology between sequences, e.g. Kafatos et al, *Nucleic Acids Research*, Vol. 7, pgs. 1541-1552 (1979), and to detect consensus sequences, e.g. Oliphant et al, *Meth. Enzymol.*, Vol. 155, pgs. 568-582 (1987). Implicit to all of these applications is the notion that the known probe sequences contain information about the unknown target sequences. This notion apparently has never been exploited to obtain detailed sequence information about a target nucleic acid.

In view of the limitations of current DNA sequencing methods, it would be advantageous for the scientific and industrial communities to have available an alternative method for sequencing DNA which (1) did not require gel electrophoretic separation of similarly sized DNA fragments, (2) had the capability of providing the sequence of very long DNA chains in a single operation, and (3) was amenable to automation.

SUMMARY OF THE INVENTION

The invention is directed to a method for determining the nucleotide sequence of a DNA or an RNA molecule using multiple mixed oligonucleotide probes. Sequence information is obtained by carrying out a series of hybridizations whose results provide for each probe the number of times the complement of the probe's sequence occurs in the RNA or DNA whose sequence is to be determined. The nucleotide sequence of the RNA or DNA is reconstructed from this information and from a knowledge of the probes' sequences. The nucleic acid whose sequence is to be determined is referred to herein as the target sequence.

The mixed oligonucleotide probes of the invention are selected from a set whose members' sequences include every possible complementary sequence to subsequences of a predetermined length within the target sequence. The series of hybridizations are separately carried out such that one or more of the probes selected from the set are combined with known quantities of the target sequence, e.g. on a nitrocellulose filter, or like substrate, under conditions which substantially allow only perfectly matched probe sequences to hybridize with the target sequence. Probe sequences having mismatched bases are substantially removed, e.g. by washing, and the quantity of perfectly matched probe remaining hybridized to the target sequence is determined.

In one embodiment of the invention, the set of probes comprises four subsets. Each of the four subsets contains probes representing every possible sequence, with respect to the size of the probe (which is predetermined), of only one of the four bases. For example, the first subset can contain probes where every possible sequence of G is represented; the second subset can contain probes where every possible sequence of T is represented; and so on for C and A. If the probes were each 8 bases long, a member probe of the adenosine subset can be represented as follows:

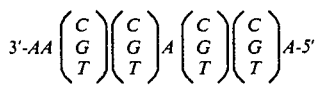

Formula I

The symbol

means that any of the bases C, G, or T may occupy the position where the symbol is located. Thus, the above probe has a multiplicity, or degeneracy, of $1\times1\times3\times3\times1\times3\times3\times1$ or 81. When it is clear from the context which subset is being considered, the above notation will be simplified to AA00A00A, where A represents deoxyadenosine and 0 represents the absence of deoxyadenosine.

Preferably, base analogs are employed in the oligonucleotide probes whose base pairing characteristics permit one to reduce the multiplicity of the probe. For example, in the probe of Formula II, because deoxyinosine (I) forms nearly equally strong base pairs with A and C, but forms only a weak or destabilizing base pair with either G or T, deoxyinosine can replace G and T in the probe, Martin et al, *Nucleic Acids Research*, Vol. 13, pgs. 8927–8938 (1985). Thus, a probe equivalent to that of Formula I, but which has a much lower multiplicity (i.e. only 16) can be represented as follows:

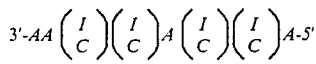

Formula II

Generally, base analogs are preferred which form strong base pairs (i.e., comparable in binding energy to the natural base pairs) with two or three of the four natural bases, and a weak or destabilizing base pair with the complement of a fixed base (defined below). Such base analogs are referred to herein as degeneracy-reducing analogs.

It is not critical that the probes all have the same length, although it is important that they have known lengths and that their sequences be predetermined. Generally, the probes will be fixed at a predetermined number of positions with known bases (not necessarily of the same kind), e.g. as the A in Formula I, and the remaining positions will each be filled by a base randomly selected from a predetermined set, e.g. T, G, and C as in Formula I, or I and C as in Formula II. The positions in a probe which are nondegenerate in their base pairing, i.e. have only a single natural base, are referred to herein as fixed positions. The bases occupying fixed positions are referred to herein as fixed bases. For example, the fixed bases in the probes of Formulas I and II are deoxyadenosine at positions one, two, five, and eight with respect to the 3' end of the probe.

Generally, sets and/or subsets of the invention each contain at least one probe having a sequence of fixed and non-fixed positions equivalent to that of each permutation of a plurality of fixed and non-fixed positions less than or equal to the length of the probe. That is, an important feature of the invention is that the probes collectively contain subsequences of fixed and non-fixed positions (which may be the total length of the probe, as is the case for the probe sequences of Appendix I) which correspond to every possible permutation of fixed and non-fixed positions of each of a plurality of combinations of fixed and non-fixed positions, the plurality including combinations containing from zero to all fixed positions. For example, consider a subset of probes of the invention that consists of 8-mer probes whose fixed positions contain only deoxyadenosine and whose initial (i.e., 3'-most) position is fixed. The probes of Formulas I and II are members of such a subset. Within such a subset, there is a leas: one probe having a subsequence of fixed and non-fixed positions in positions 2 through 8 which corresponds to each possible permutation of fixed and non-fixed positions for subsequences having no fixed positions (one such permutation: A0000000), one fixed position (seven such permutations, e.g. A000A000), two fixed positions (twenty-one such permutations, e.g. A00AA000), three fixed positions (thirty-five such permutations, e.g. A00-00AAA), four fixed positions (thirty-five such permutations, e.g. A0AAAA00), five fixed positions (twenty-one such permutations, e.g. AAA00AAA), six fixed positions (seven such permutations, e.g. AAAA0AAA), and seven fixed positions (one such permutation: AAAAAAAA). Thus, the subset has at least $1+7+21+35+35+21+7+1=128$ members.

The presence of one or more predetermined known sequence regions in the target sequence facilitates the reconstruction of the target sequence. Accordingly, in a preferred embodiment, the target sequence contains one or more regions of known sequence, these regions being referred to herein as known sequence regions. More preferably, the target sequence contains a first and a second known sequence region, the first and second known sequence regions being positioned on opposite ends of the region of the target sequence containing the unknown sequence of nucleotides. This unknown sequence of nucleotides is referred to herein as the unknown sequence region. Most preferably, the first and second known sequence regions are at least the length of the longest probe sequence.

Besides a method of sequencing nucleic acids, the invention also includes kits and compositions including vectors and mixtures of oligonucleotides for constructing probes for use in accordance with the method of the invention. Oligonucleotide mixtures of the invention have sequences of fixed and non-fixed bases. Preferably, such mixtures comprise sequences represented by the formula:

$$X_{i1}X_{i2}X_{i3}\ldots X_{in}$$

wherein:

$i_1$ through $i_n$ are separately either 0 or 1;

$X_0$ represents a non-fixed base;

$X_1$ represents a fixed base; and n is in the range of from 6 to 10.

More preferably, whenever $X_1$ represents A, $X_0$ is selected from the group consisting of C, G, T, and degeneracy-reducing analogs thereof; whenever $X_1$ represents C, $X_0$ is selected from the group consisting of A, G, T, and degeneracy-reducing analogs thereof; whenever $X_1$ represents G, $X_0$ is selected from the group consisting of A, C, T, and degeneracy-reducing analogs thereof; and whenever $X_1$ represents T, $X_0$ is selected from the group consisting of A, C, G, and degeneracy-reducing analogs thereof.

BRIEF DESCRIPTION OF THE DRAWINGS

FIG. 1 illustrates the general problem of sequence reconstruction by showing how a 21-mer sequence can be reconstructed by four subsets of 4-mer probes.

FIG. 2 is a flow chart diagrammatically illustrating a preferred reconstruction algorithm.

DETAILED DESCRIPTION OF THE INVENTION

The present invention provides a method of nucleotide sequence determination which takes advantage of the extremely specific hybridization behavior of oligonucleotides. Easily synthesized oligonucleotide probes from a predetermined set are separately hybridized to known quantities of a target sequence so that the number of copies of perfectly matched probe on the target sequence can be determined. Once such a determination is made for each probe of the predetermined set, the target sequence can be reconstructed by a mathematical algorithm.

I. Composition and Labeling of the Probes

Mixed oligonucleotide probes for the invention are preferably synthesized using an automated DNA synthesizer, e.g. Applied Biosystems (Foster City, CA) models 381A or 380B, or like instrument. At nonfixed positions mixtures of the appropriate nucleotide precursors are reacted with the growing oligonucleotide chain so that oligonucleotides having different bases at that position are synthesized simultaneously, e.g. as disclosed by Wallace et al, *Nucleic Acids Research*, Vol. 6, pgs. 3543-3557 (1979), and Oliphant et al, *Meth. Enzymol.*, Vol. 155, pgs. 568-582 (1987).

The probes may be synthesized by way of any of the available chemistries, e.g. phosphite triester, Beaucage et al, *Tetrahedron Letters*, Vol. 22, pgs. 1859-1862 (1981); Caruthers et al, U.S. Pat. Nos. 4,415,723, 4,458,066, and 4,500,707; phosphotriester, Itakura, U.S. Pat. No. 4,401,796; hydrogen phosphonate, e.g. Froehler et al, *Nucleic Acids Research*, Vol. 14, pgs. 5399-5407 (1986); or the like. It is not critical that the bases of the probes be linked by phosphate esters. Analogs of the natural phosphate ester linkages can be used, e.g. Jones, *Int. J. Biol. Macromol.*, Vol. 1, pgs. 194-207 (1979), reviews synthetic analogs of phosphate esters; and Ts'o et al, U.S. Pat. No. 4,469,863 describe the synthesis of alkyl and aryl phosphonate analogs. Probes of the invention can also comprise oligoribonucleotides, e.g. Ebe et al., *DNA*, Vol. 6, pgs. 497-504 (1987).

Once synthesized, the oligonucleotides are purified for labeling by well known techniques, usually HPLC or gel electrophoresis, e.g. *Applied Biosystems DNA Synthesizer Users Bulletin*, Issue No. 13-Revised (Apr. 1, 1987); or Gait, ed., *Oligonucleotide Synthesis: A Practical Approach* (IRL Press, Washington, D.C., 1984). Alternatively, the oligonucleotides for the probe can be purified by affinity chromatography using oligonucleotides complementary to the probe sequences covalently attached to a suitable solid phase support, e.g. Gilham, *J. Amer. Chem. Soc.*, Vol. 86, pg. 4982 (1964); and Kremsky et al, *Nucleic Acids Research*, Vol. 15, pgs. 3131-3139 (1987).

Selecting the lengths of the probes is an important aspect of the invention. Several factors influence the choice of length for a given application, including (1) the ease with which hybridization conditions can be manipulated for preferentially hybridizing probes perfectly matched to the target sequence, (2) the ability to distinguish between roughly integral amounts of perfectly matched probe hybridized to the target sequence (e.g. if the probe is relatively long so that the expected frequency of probe sequences perfectly complementary to the target is low, one may be required to distinguish (for example) between amounts of probe in the range of 10, 20, or 30 picomoles—to infer that 1, 2, or 3 copies of the probe are present on the target; if the probe is relatively short so that the expected frequency of probe sequences perfectly complementary to the target is high, one may be required to distinguish (for example) between amounts of probe in the range of 110, 120, or 130 picomoles—to infer that 11, 12, or 13 copies of the probe are present on the target; since the fractional differences between the latter quantities are small, there may be less confidence in the inferred copy number); (3) whether probe multiplicity permits hybridization with reasonable Cot values (longer probes are more degenerate than shorter probes, and require higher Cot values for hybridization, the converse is true of shorter probes); (4) the practicality of carrying out separate hybridizations for each type of probe (longer probes give rise to larger sets of probes, e.g. probes having permutations of fixed and non-fixed bases in seven positions give rise to a set of $2^7-1$, or 127 probes, for each kind of base, for eight positions this number is $2^8-1$, or 255, and so on); and (5) the tractability of the sequence reconstruction problem (the greater the number of copies of each probe type on the target sequence—which is the tendency if shorter probes are employed, the more difficult the reconstruction problem). Probe sizes in the range of 7 to 11 bases are preferred. More preferably, probes sizes are in the range of 8 to 10 bases, and most preferably, probe sizes are in the range of 8 to 9 bases.

Preferably, degeneracy-reducing analogs are employed at the non-fixed positions of the probes to reduce probe multiplicity, or degeneracy. Many synthetic and natural nucleoside and nucleotide analogs are available for this purpose, e.g. Scheit, *Nucleotide Analogs* (John Wiley & Sons, N.Y., 1980). For example, degeneracy-reducing analogs include deoxyinosine for use in cytosine or adenosine probes to replace G and T at non-fixed positions, 2-aminopurine for use in cytosine or guanosine probes to replace A and T at non-fixed positions, and $N^4$-methoxydeoxycytidine, $N^4$-aminodeoxycytidine, or 5-fluorodeoxyuridine for use in adenosine or guanosine probes to replace T and C. Use of deoxyinosine in oligonucleotide probes is disclosed by Martin et al (cited above); Seela et al, *Nucleic Acids Research*, Vol. 14, pgs. 1825-1844 (1986); Kawase et al, *Nucleic Acids Research*, Vol. 14, pgs. 7727-7737 (1986); Ohtsuka et al, *J. Biol. Chem.*, Vol. 260, pgs. 2605-2608 (1985); and Takahashi et al, *Proc. Natl. Acad. Sci.*, Vol. 82. pgs. 1931-1935 (1985). Accordingly, these references are incorporated by reference. Deoxyinosine phosphoramidite precursors for automated DNA synthesis are available commercially, e.g. Applied Biosystems (Foster City, Calif.). The synthesis of $N^4$-methoxycytidine and its incorporation into oligonucleotide probes is disclosed by Anand et al, *Nucleic Acids Research*, Vol. 15, pgs. 8167-8176 (1987). The synthesis of 2-aminopurine and its incorporation into oligonucleotide probes is disclosed by Eritja et al, *Nucleic Acids Research*, Vol. 14, pgs. 5869-5884 (1986). The synthesis of 5- fluorodeoxyuridine and its incorporation into oligonucleotide probes is disclosed by Habener et al, *Proc. Natl. Acad. Sci.*, Vol. 85, pgs. 1735-1739 (1988). And the preparation of N⁴-aminodeoxycytidine is disclosed by Negishi et al, *Nucleic Acids Research*, Vol. 11, pgs. 5223-5233 (1983). Accordingly, these latter four references are incorporated by reference.

Nucleoside analogs are also employed in the invention to reduce the differences in binding energies between the various complementary bases. In particular, 2-aminoadenine can replace thymine in either the probe or target sequences to reduce the binding energy differences between A-T nucleoside pairs and G-C nucleoside pairs, e.g. Kirnos et al (cited above), Chollet et al (cited above), and Cheong et al, *Nucleic Acids Research*, Vol. 16, pgs. 5115-5122 (1988). Procedures for synthesizing oligonucleotides containing 2-aminoadenine are disclosed by Chollet et al (cited above); Gaffney et al, *Tetrahedron*, Vol. 40, pgs. 3-13 (1984), and Chollet et al *Chemica Scripta*, Vol. 26, pgs. 37-40 (1986). Likewise, 2-amino-2'-deoxyadenosine can replace deoxyadenosine to increase the binding Dihn et al, *Proc. Natl. Acad. Sci.*, Vol. 82, pgs. 7510-7514 (1985).

In some embodiments, it may be preferable to replace a more degenerate probe with several less degenerate probes which collectively are capable of obtaining the same information about the target sequence. For example, consider the 9-mer probe A00000000. This probe can be replaced by the three less degenerate probes A0000000C, A0000000G, and A0000000T. Thus, at the cost of two additional hybridizations, the degeneracy of the most degenerate probe in the set is reduced from 256 to 128 (assuming the use of deoxyinosine at non-fixed positions).

The oligonucleotides of the invention can be labeled in a variety of ways to form probes, including the direct or indirect attachment of radioactive moieties, fluorescent moieties, electron dense moieties, and the like. It is only important that each sequence within a probe be capable of generating a signal of the same magnitude, so that quantitative measurements of probe number can be made. There are several means available for derivatizing oligonucleotides with reactive functionalities which permit the addition of a label. For example, several approaches are available for biotinylating an oligonucleotide so that fluorescent, enzymatic, or electron density labels can be attached via avidin: Broken et al, *Nucleic Acids Research*, Vol. 5, pgs. 363-384 (1978), disclose the use of ferritin-avidin-biotin labels; Chollet et al, *Nucleic Acids Research*, Vol. 13, pgs. 1529-1541 (1985), disclose biotinylation of the 5' termini of oligonucleotides via an aminoalkylphosphoramide linker arm; and Bayer et al, *Methods of Biochemical Analysis*, Vol. 26, pgs. 1-45 (1980) provide a general review of the use of the avidin-biotin complex. Several methods are also available for synthesizing amino-derivatized oligonucleotides which are readily labeled by fluorescent or other types of compounds derivatized by amino-reactive groups, such isothiocyanate, N-hydroxysuccinimide, or the like, e.g. Connolly, *Nucleic Acids Research*, Vol. 15, pgs. 3131-3139 (1987); Gibson et al, *Nucleic Acids Research*, Vol. 15, pgs. 6455-6467 (1987); Miyoshi et al, U.S. Pat. No. 4,605,735. Methods are also available for synthesizing sulfhydryl-derivatized oligonucleotides which can be reacted with thiol-specific labels, e.g. Connolly, *Nucleic Acids Research*, Vol. 13, pgs. 4485-4502 (1985); and Spoat et al, *Nucleic Acids Research*, Vol. 15, pgs. 4837-4848 (1987). A comprehensive review of methodologies for labelling DNA probes is provided by Matthews et al, *Anal. Biochem.*, Vol 169, pgs. 1-25 (1988).

Alternatively, probes of the invention can generate a signal indirectly using a detection scheme disclosed by Sutherland et al, European patent application publication number 245206. In this embodiment, probe sequences are anchored to the end of a fiber optic so that they are free to hybridize to target sequences, which have been broken up into segments and denatured, e.g. by random endonuclease digestion and boiling, to facilitate hybridization. (In this embodiment the probe sequences, not the target sequences, are anchored to a solid phase substrate). Upon hybridization of the probe and target sequences the duplex is detected by fluorescence generated by an intercalating dye, e.g. ethidium bromide, which is transmitted along the fiber optic to a photodetector.

In one preferred embodiment of the invention, the probes are biotinylated, e.g. as taught by Chollet et al (cited above), and after hybridization and washing, the probes are reacted with avidin or streptavidin conjugated to a fluorescent dye or one or more enzyme molecules for generating a colorimetric signal. Preferred fluorescent dyes include fluorescein, tetramethylrhodamine, rhodamine, phycorythrin, Texas Red, and the like.

In another preferred embodiment, the oligonucleotides of the invention are radioactively labeled with $^{32}P$ using standard protocols, e.g. Maniatis et al, *Molecular Cloning: A Laboratory Manual* (Cold Spring Harbor Laboratory, N.Y., 1982); *Current Protocols in Molecular Biology*, Unit 6.4 (John Wiley & Sons, N.Y., 1987); or. Maxim and Gilbert, *Meth. Enzymol.*, Vol. 65, pgs. 499-560 (1980). $^{32}P$-labeled probes of the invention are preferably applied to tangent DNAs anchored to nitrocellulose, nylon, or the like, at a concentration in the range of about 1-10 ng/ml, and more preferably, in the range of about 1-5 ng/ml. The specific activities of the probe are preferably in the range of about $1-5 \times 10^6$ cpm/ml.

II. Hybridization

The hybridizations of the probes to the target sequence are carried out in a manner which allows mismatched probe sequences and nonspecifically bound probe sequences to be separated from the duplexes formed between the perfectly matched probe sequences and the target sequence. Usually the separation is carried out by a washing step. Preferably, the first step in the hybridizations is to anchor the target sequence so that washes and other treatments can take place with minimal loss of the target sequences. The method selected for anchoring the target sequence depends on several factors, including the length of the target, the method used to prepare copies of the target, and the like. For example, DNA sequences less than 200-300 bases in length do not bind efficiently to nitrocellulose, Meinkoth et al, *Anal. Biochem.*, Vol. 138, pgs. 267-284 (1984); thus, for shorter target sequences alternatives to nitrocellulose may be preferable, such as covalent binding to diazotized paper, e.g. Alwine et al, *Proc. Natl. Acad. Sci.*, Vol. 74, pgs. 5350-5354 (1977); or Rabbani, U.S. Pat. No. 4,139,346 (which patent is incorporated by reference); covalent attachment to derivatized microspheres, e.g. Kremsky et al, *Nucleic Acids Research*, Vol. 15, pgs. 2891-2909 (1987); or attachment to a derivatized nylon substrate, such as Zeta Probe (a trademarked product of Bio-Rad) or GeneScreen (a trademarked product of New England Nuclear). When targets are about 1.5 kilobases or larger they can be anchored in a gel matrix, e.g. as disclosed by Miyada et al, *Meth. Enzymol.*, Vol. 154, pgs. 94–107 (1987).

The selection of appropriate prehybridization, hybridization, and wash conditions for particular embodiments depends on several factors, including the length of the probe, the degeneracy of the probe, the nature of the bases and/or base analogs making up the probe, the means employed for anchoring the target sequence, and the like. A great deal of literature is available for guidance in selecting prehybridization, hybridization, and washing conditions in view of the above factors for particular embodiments, e.g. Wetmur et al, *J. Mol. Biol.*, Vol. 31, pg. 349 (1968); Meinkoth et al, *Anal. Biochem.*, Vol. 138, pgs. 267–284 (1984); Eritja et al, *Nucleic Acids Research*, Vol 14, pgs. 8135–8153 (1986); Aboul-ela et al, *Nucleic Acids Research*, Vol. 13, pgs. 4811–4824 (1985); Millican et al, *Nulceic Acids Research*, Vol. 12, pgs. 7435–7452 (1987); Ikuta et al, *Nucleic Acids Research*, Vol. 15, pgs. 797–811 (1987); Kawase et al, *Nucleic Acids Research*, Vol. 14, pgs. 7727–7736 (1985); Seela et al, *Nucleic Acids Research*, Vol 14, pgs. 1825–1844 (1986); Anand et al, *Nucleic Acids Research*, Vol. 8167–8177 (1987); Gingeras et al, *Nucleic Acids Research*, Vol. 15, pgs. 5373–5390 (1987); Miyada et al, *Meth. Enzymol.*, Vol. 154, pgs. 94–107 (1987); Ohtsuka et al, *J. Biol. Chem.*, Vol. 260, pgs. 2605–2608 (1985); Kafatos et al, *Nucleic Acids Research*, Vol. 7, pgs. 1541–1552 (1979); Wood et al, *Proc. Natl. Acad. Sci.*, Vol. 82, pgs. 1585–1588 (1985); and Wallace et al, *Nucleic Acids Research*, Vol. 6, pgs. 3543–3557 (1979). Accordingly, these references are incorporated by reference.

When the target sequence is in the range of about 400–1500 bases in length, the preferred anchoring means is nitrocellulose or derivatized nylon, such as GeneScreen, ZetaProbe, or the like. When the target sequence is in the range of about 100 bases to several kilobases in length, a preferred anchoring means is a nylon substrate, such as GeneScreen or GeneScreen Plus, trademarked products of New England Nuclear (Boston, Mass.), disclosed in U.S. Pat. No. 4,455,370, which is incorporated by reference. A known quantity of single or double stranded copies of the target sequence is anchored to the substrate, or solid phase support. As used herein "known quantity" means amounts from which integral numbers of perfectly matched probes can be determined. In some embodiments this means known gram or molar quantities of the target sequence. In other embodiments, it can mean equal amounts of target sequence on the plurality of solid phase supports, so that signal is corresponding to integral numbers of probes can be discerned by comparing signals from the plurality of supports, or by comparing signals to specially provided standards.

Preferably, the anchoring means is loaded to capacity with the target sequence so that maximal signals are produced after hybridization. The target sequence can be prepared in double stranded form, denatured, and then applied to the anchoring means, which is preferably a solid phase support, such as nitrocellulose, GeneScreen, or the like. When the target sequence is prepared in double stranded form, it is preferably excised from its cloning vector with one or more endonucleases which leave blunt ended fragments, e.g. Eco RV, Alu I, Bal I, Dra I, Nae I, Sma I, or the like. In this case, both the coding, or sense, strand and the noncoding, or antisense, strand are sequenced simultaneously. Because of sequence complementarity, the reconstruction problem is no more difficult than in the single stranded case. In some cases, an independent test or internal standard may be required to determine which of the two reconstructed sequences is the coding strand. An internal standard can comprise the inclusion of a known sequence of nucleotides within the two strands that are sequenced.

Suitable vectors for preparing double stranded target sequences are those of the pUC series, e.g. Yanisch-Perron et al, *Gene*, Vol. 33, pgs. 103–119 (1985). These vectors are readily modified by adding unique restriction sites to their polylinker regions. The new unique restriction sites are selected from restriction endonucleases that leave flush-ended fragments after digestion. For example, chemically synthesized fragments containing such sites can be inserted into the Hind III and Eco RI sites of pUC18 or pUC19. For these vectors such sites include Bal I, Eco RV, Hpa I, Nae I, Nru I, Stu I, Sna BI, and Xca 1. With the modified pUC, the precursor of the target sequence (i.e. the unknown sequence region) can be inserted into a preexisting polylinker site, e.g. Bam HI; the vector can be amplified and isolated; and the target sequence can be excised via the restriction endonucleases that leave flush-ended fragments. The fragments of the polylinker region excised along with the unknown sequence region then become the known sequence regions of the target sequence.

Single stranded target sequences can be prepared in the form of RNA using an SP6 promoter system, or similar system, as disclosed by Melton et al, *Nucleic Acids Research*, Vol. 12, pgs. 7035–7056 (1984). SP6-based systems, and related systems, are commercially available from Promega Corporation (Madison, Wis.) as Riboprobe vectors, and United States Biochemical Corporation (Cleveland, Ohio) as GeneScribe vectors. RNA target sequences can be prepared with the SP6-like vectors in several ways. For example, the double stranded DNA form of a target sequence can be inserted into a cloning vector and amplified. The vector is then isolated and linearized by digesting with the enzyme corresponding to the restriction site at the 3' end of the target sequence insert. RNA polymerase is used to generate RNA copies of the coding strand of the target sequence. Alternatively, the target sequence can be inserted into the SP6 (or related) vector in tandem with a transcription termination sequence, which blocks RNA polymerase. Thus, the linearization step is not required. Appropriate transcription terminatiors are disclosed by Belagaje et al, U.S. Pat. No. 4,710,464. Accordingly, that patent is incorporated by reference.

Copies of the target sequence can also be generated by way of a polymerase chain reaction, e.g. Saiki et al, *Science*, Vol. 230, pgs. 1350–1354 (1985); Wrischnik et al, *Nucleic Acids Research*, Vol. 15, pgs. 529–542 (1987); U.S. Pat. Nos. 4,683,195 and 4,683,202. Accordingly, these references are incorporated by reference. In particular, single stranded copies can be obtained by providing a first primer in the standard two primer amplification scheme (1) that is longer than the second primer and (2) that contains a 5' region noncomplementary to its target strand. This results in so-called "short products" of unequal length which can be denatured and separated by size after amplification (e.g. as discussed below).

Single stranded target sequences can also be prepared by separating the complementary strands of the double stranded DNA by RPC-5 chromatography under denaturing conditions, e.g. Eshaghpour et al, *Nucleic Acids Research*, Vol. 5, pgs. 13-21 (1978), and Wells et al, *Meth. Enzymol.*, Vol. 65, pgs. 327-347 (1980). Accordingly, these references are incorporated by reference.

The preferred method of anchoring DNA to nitrocellulose filters is essentially that described by Kafatos et al (cited above). Up to about 1 ug of target sequence is applied per square millimeter of the filter. Before application the DNA is denatured, preferably in 0.3 to 0.4 N NaOH for about 10 minutes, after which it is chilled with an equal volume of cold water, or optionally cold 2 M ammonium acetate, to a concentration of about 16 ug/ml. Known quantities of the denatured target are spotted onto the filter by carefully controlling the volume of liquid deposited. After each sample is spotted (approximately 1.5 minutes), the filter can optionally be rinsed through with a drop of 1 M ammonium acetate containing about 0.02-0.2 N NaOH, pH 7.8-9.0. Filters may also be washed with 4×SSC (defined below), e.g. about 200 ml. The filters are air dried, shaken in 2× Denhardt's solution (defined below) for at least 1 hour, drained and air dried again, and baked under vacuum at 80° C. for about 2 hours.

Hybridization of the probes to the target sequence usually comprises three steps: a prehybridization treatment, application of the probe, and washing. The purpose of the prehybridization treatment is to reduce nonspecific binding of the probe to the anchoring means and non-target nucleic acids. This is usually accomplished by blocking potential nonspecific binding sites with blocking agents such as proteins, e.g. serum albumin (a major ingredient of Denhardt's solution). The commonly used blocking agent, denatured sonicated salmon sperm DNA, is usually not appropriate with the present invention. Such a blocking agent could be a source of specific and nonspecific binding sites because of the short length of the probes. Any blocking agent comprising natural DNA has a high probability of containing some complementary sequences to some probes. However, non-labelled oligonucleotide mixtures specially selected to be maximally noncomplementary to the probe sequence can be prepared for subsets of the probes for use as blocking agents.

For example, probes of the form

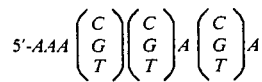

would be maximally noncomplementary to a probe of the form 3'-

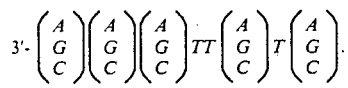

For target sequences anchored to nitrocellulose or nylon (e.g. GeneScreen), prehybridization treatment can comprise treatment with 5-10x Denhardt's solution, with 2-6x SSC preferably containing a mild detergent, e.g. 0.5% sodium dodecylsulfate (SDS), for 15 min. to 1 hr. at a temperature in the range of about 25° to 60°. Denhardt's solution, disclosed in *Biochem. Biophys. Res. Commun.*, Vol. 23, pgs. 641-645 (1966), consists at 10x concentration of 0.2% bovine serum albumin, 0.2% polyvinylpyrolidone, and 0.2% Ficoll. SSC, another standard reagent in the hybridization art, consists at 1x of 0.15 M NaCl, 0.015 M sodium citrate, at pH 7.0. Preferred treatment times, temperatures, and formulations may vary with the particular embodiment.

Preferably, the probe is applied to the anchored DNA at a concentration in the range of about 1-10 ng/ml in a solution substantially the same as the prehybridization solution, e.g. 5-10x Denhardt's solution with 2-6x SSC and a mild detergent, e.g. 0.5% SDS. More preferably, the probe concentration is in the range of about 1-5 ng/ml. Preferably, the hybridization is carried out at a temperature 10-20° C. below the expected 50% dissociation temperature, $T_d$, between the probe and the target. That is, a temperature is selected at which a high proportion, e.g. greater than 80-90%, of all the perfectly matched probes form stable duplexes. For 8-mer probes the preferred hybridization temperature is in the range of about 10-18° C. Hybridization times are preferably in the range of about 3-16 hours. Different hybridization times may be selected for probes of different degrees of degeneracy, because the effective consentrations of particular sequences within a highly degenerate probe, e.g. 0A000000, are considerably less than those of particular sequences in a low degeneracy probe, e.g. AAA0AAAA. Thus, higher Cot values (which usually means longer hybridization times) may be required for more degenerate probes to attain a sufficient degree of binding of perfectly matched sequences. Preferably, a single hybridization time is selected for all probes which is determined by the hybridization kinetics of the most degenerate probe. Probe degeneracy becomes important when relative signals are compared after autoradiography. Probes having higher degeneracy will produce lower signals than probes of lower degeneracy. Therefore, relative signals should only be compared among autoradiographs associated with probes of equivalent degeneracy. Signal comparisons are aided by the simultaneous running of positive and negative controls for each probe, or at least for each degeneracy class.

Removing nonspecifically bound and mismatched probe sequences by washing is an important aspect of the invention. Temperatures and wash times are selected which permit the removal of a maximum amount of nonspecifically bound and mismatched probe sequences, while at the same time permit the retention of a maximum number of probe sequences forming perfectly matched duplexes with the target. The length and base composition of the probe are two important factors in determining the appropriate wash temperature. For probe lengths in the preferred range of 7-11 bases, the difference in duplex stability between perfectly matched and mismatched probe sequences is quite large, the respective $T_d$'s differing by perhaps as much as 10° C., or more. Thus, it is not difficult to preferentially remove mismatches by adjusting wash temperature. On the other hand, composition differences, e.g. G-C content versus A-T content, give rise to a broadened range of probe $T_d$'s, and lower wash temperatures reduce the ability to remove nonspecifically bound probe. Consequently, the wash temperature must be maximized for removing nonspecifically bound probe, yet it cannot be so high as to preferentially remove perfectly matched probes with relatively high A-T content.

Preferably, hybridization conditions and/or nucleotide analogs are selected which minimize the difference in binding energies of the various base pairs, in order to minimize sequence-specific differences in probe binding. Such minimization is preferable because it increases the sensitivity with which perfectly matched probes can be detected. Sensitivity is increased because such minimization makes the transition from probe/target duplexes to single stranded probe and single stranded target much sharper when temperature is increased, i.e. the probe/target $T_m$ is less broad. For example, when hybridization occurs in the presence of tetraalkylammonium salts, the differences in binding energy between G-C pairs and A-T pairs is reduced, e.g. Wood et al, *Proc. Natl. Acad. Sci.*, Vol. 82, pgs. 1585-1588 (1985); and Melchior et al, *Proc. Natl. Acad. Sci.*, Vol. 70, pgs. 298-302 (1973). Likewise, use of alpha-anomeric nucleoside analogs results in stronger binding energies, e.g. Moran et al, *Nucleic Acids Research*, Vol. 16, pgs. 833-847 (1988); and the use of 2-aminoadenine in place of adenine results in stronger binding, e.g. Chollet et al, *Nucleic Acid Research*, Vol 16, pgs. 305-317 (1988). Accordingly, a preferred wash procedure for 8-mer probes comprises washing the filters three times for about 15 minutes in 6x SSC containing 0.5% SDS at a temperature in the range of about 10-12° C., followed by one or two rinses with 3.0 M Me4NCl, 50 mM Tris-HCl, pH 8.0, 0.5% SDS, at a temperature in the range of about 10-12° C., followed by a 1.5-2.5 minute wash in 3.0 M Me4NCl, 50 mM Tris-HCl, pH 8.0, 0.5% SDS, at a temperature in the range of about 24-28° C. For 9-mer probes, the procedure is substantially the same, except that the final wash temperature is preferably in the range of about 26-30° C.

After hybridization and washing, quantitative measurements of bound probe are carried out using standard techniques, e.g. for radiolabelled probes, autoradiography or scintillation counting can be used. In some cases, an intensifying screen, or solution, may be preferred to amplify the signal from the radioactive probe, e.g. Shine et al, *Anal.Biochem.*, Vol. 59, pgs. 360-365 (1974). After exposure to a suitable film, relative amounts of probe can be determined by a densitometer, e.g. Bio-Rad model 620, or the like.

III. Sequence Reconstruction

The general nature of the reconstruction problem is illustrated by the example of FIG. 1, in which four subsets of 4-mer probes are used to analyze the sequence of the 21-mer, CGAATGGAACTACCGTAACCT. On the left of FIG. 1 is a list of 4-mer probes having every possible permutation of fixed and non-fixed positions with respect to deoxyadenosine, deoxycytcsine, deoxyguanosine, and thymidine, respectively, for the following combinations of fixed bases and non-fixed bases: 1 fixed and 3 non-fixed, 2 fixed and 2 non-fixed, 3 fixed and 1 non-fixed, and 4 fixed and 0 non-fixed. That is, the list contains at least one probe having a sequence of fixed and nonfixed positions with respect to A, C, G, and T equivalent to every possible permutation of A's and non-fixed positions, C's and non-fixed positions, G's and non-fixed positions, and T's and non-fixed positions, respectively. In the figure, there is one probe for each row of a two dimensional array having a number of columns equal to the length of the unknown sequence, in this example 21. The data obtained by listed under the column, "Perfect Matches." The data represent the number of each probe type having perfect complementarity with a four base subsequence of the 21-mer. Under the 21-mer sequence itself the probes are positioned along the sequence where perfect complementarity occurs. The objective of a reconstruction algorithm is to determine the positions of enough probes so that the target sequence can be reconstructed.

The reconstruction problem can be approached in many ways. The problem is related to the traveling salesman problem in that it involves finding a permutation of objects which is in some sense optimal. There is an extensive literature on such combinatorial problems which provides guidance in formulating the best approach for a particular embodiment, e.g. Lawler, *Combinatorial Optimization: Networks and Matroids*, (Holt, Rinehart, and Winston, N.Y., 1976); Lawler et al, eds., *The Traveling Salesman Problem: A Guided Tour of Combinatorial Optimization* (John Wiley & Sons, N.Y., 1985); Kirkpatrick, *J. Stat. Phys.*, Vol. 34, pgs. 975-986 (1984); Kirkpatrick et al, *Science*, Vol. 220, pgs. 671-680 (1983); Held and Karp, *J. Soc. Indust. Appl. Math.*, Vol. 10, pgs. 196-210 (1962); Lin and Kernighan, *Oper. Res.*, Vol 21, pgs. 498-516 (1973); and Gonzalez, MIT Interim Technical Report No. 18 (May, 1962).

One approach to creating a reconstruction algorithm is to examine the conditions that a solution must satisfy. In the example of FIG. 1, a necessary condition for the correct positioning of the probes is that the fixed bases of each probe subset, say deoxyadenosine, never overlap the fixed bases of another probe subset, e.g. thymidine, deoxycytosine, or deoxyguanodine. Note in FIG. 1 that A's overlap only 0's or other A's, C's overlap only 0's or other C's, and so on. Thus, one way to reconstruct the 21-mer is to shift the copies of each probe sequence (or a subset thereof) along their respective rows until a configuration is found such that whenever different probe sequences overlap, i.e. occupy the same column or columns, each column contains only A's and 0's, only C's and 0's, or only T's and 0's (like the configuration illustrated in FIG. 1).

A preferred approach to the reconstruction problem requires that the target sequence include one or more known sequence regions. In particular, a first known sequence region is located at one end of the target sequence and a second known sequence region is located at the other end of the target sequence. The presence of the two known sequence regions permits the construction of a simplified and efficient reconstruction algorithm. Roughly, the reconstruction problem is a problem of finding an ordering of overlapping probe sequences which corresponds to the target sequence. The known sequence regions define the starting and ending probes sequences in a reconstruction. The intervening unknown sequence region can be reconstructed from the remaining probe sequences by requiring that each successively selected probe properly overlap the previously selected probe sequence. FIG. 2 is a flow chart of such an algorithm. It consists of two parts which are performed alternatively, drawing probes from the same set (referred to herein as the data set) determined by the hybridization data: (1) construction of candidate sequences from properly overlapping fixed-initial-position and fixed-final position probes starting from one of the known sequence regions, and (2) construction of candidate sequences from properly overlapping fixed-final-position and fixed-initial-position probes starting from the other known sequence region. The term "properly overlapping" simply means overlapping in the sense described at the beginning of this section and illustrated in FIG. 1. Thus, in this algorithm only probes having either a fixed initial position (3') or a fixed final position (5'), or both, are employed in the reconstruction. These two classes of probes are referred to herein as FIP probes and FFP probes.

For the algorithm, two sets of numbers (or logical variables depending on the implementation) are defined by the nucleotide sequences of the first and second known sequence regions. These sets are referred to as the initial left register and the initial right register 2, respectively. The size of the registers depends on the length of the probes employed. Usually the registers have L−1 elements, or entries, where L is the length of the probe. Starting with the initial right register, the algorithm compares the entries of the register with every FFP and FIP probe that forms a perfect match with the target sequence, 4. The comparison is between bases 2 through L of the selected probe and the numbers (or entries) 1 through L−1 of the right register. That is, base at position 2 is compared to the entry at position 1 of the right register, base at position 3 is compared to the entry at position 2 of the right register, and so on. Initially, as stated above, the entries of the registers are determined by the bases of the first and second known sequence regions. If the comparison results in proper overlap in each of the L−1 positions, then the current contents of the register are loaded into a new right register and then the entries of the new right register are shifted to the right one position. That is, entry 1 of the new right register is moved to position 2, entry 2 is moved to position 3, and so on. Entry L−1 is discarded, and the fixed base at the initial position of the probe (or some representation of it) is loaded into position 1. Next, for the new right register and selected probe to be retained for further comparisons, an FFP probe must be found that properly overlaps the register and the initial fixed base of the selected FIP probe (unless of course the FIP probe is also an FFP probe) 8. When such selections are made (i.e. 4 and 8) the selected probe(s) are removed from the data set. The new right register is saved along with and associated set of properly overlapping FIP probes whose selections led to the current register, and an associated set of properly overlapping FFP probes.

After each new right register is formed, one or more left registers are formed, 16 and 18, by extending preexisting left registers in substantially the same way as the right registers, excepts that FFP probes are selected first and positions 1−L of the FFP probe are compared to entries 1−L of the left register. The FIP and FFP probes are selected from the probes remaining in the data set. That is, any probes previously selected to "extend" the right or left registers cannot be selected. This also holds for right registers formed in successive iterations after the first. As a result of these comparisons, pairs of right and left registers are formed, and associated with each pair are four sets of probes, 20: (i) the set of FIP probes selected to extend the right register, (ii) the set of FFP probes selected to properly overlap the right register and FIP probe, (iii) the set of FFP probes selected to extend the left register, and (iv) the set of FIP probes selected to properly overlap the left register and FFP probe. At each step i (see FIG. 2), $M_{i+1}$ such pairs and associated sets are formed.

The comparisons between probe and register positions are carried out as follows. The register entries are always the bases A, C, G, or T (or some representation thereof). The probe positions are always occupied by a base or the absence of a base. Recall from above that probes can be represented by the notation, for example, A0AA000A. The 0's represent in this case represent either C, G, T, or a degeneracy-reducing analog thereof. In other words, the 0's represent "not A's". The comparisons entail the determination of the truth value of a base (from the register) and a base or a negative of a base (from the probe being compared). For example, if the register entry is A and the probe entry is "not T", then the logical operation of "A AND not T" is logically true. Thus, proper overlap exists. On the other hand, is the probe entry is "not A", then the logical operation of "A AND not A" is logically false. Thus, the overlap is improper and the probe is rejected.

In successive steps, each of the $M_i$ pairs of registers are compared to probes of their respective data sets, generating in turn, a set of $M_{i+1}$ pairs of registers. With each step the data set is reduced in size by two or more probes, and the respective canditate sequences are increased in size by one base each. When a register is compared to each of the remaining probes in its associated data set and no probe is found that properly overlaps, the register and its associated sets are discarded 6-4. The algorithm halts when every probe in the data sets have been used (i.e., sorted into one of the four associated sets). If more than one candidate sequences are generated, or if it is desired to check the consistency of the data, the same process of repeated rounds of comparisons can be carried out starting with the initial left register and set of probes that have fixed final positions and a perfect match with the target sequence 10-16. In this case, entries 1 through L−1 of the initial left register are compared with probe positions 1 through L−1, respectively, and successive registers, $R_j$ after the jth round of comparisons, are generated by shifting current entries to the left and entering the final fixed base of the properly overlapping probe to position L−1 of the new register. In a similar manner to that described above, additional candidate sequences are generated, and are compared to the ones previously generated. Only ones that occur in both sets are retained 18. Further eliminations are possible by requiring that all of the remaining non-fixed final and non-fixed initial position probes find properly overlapping positions within each of the candidates 20.

There are obvious variations of this algorithm. For example, additional known sequence regions can be embedded in the target sequence. Or, different classes of probes can be used to generate candidate sequences, e.g. probes having fixed bases at the second position, or the like.

The above algorithm does not necessarily give a unique solution in every case. Generally, regions of high frequency repeats (e.g. ACACACAC . . . , GTCGTCGTC . . . , or the like) or constant regions (e.g. AAAAAAA . . . , or the like) substantially longer than the probe give rise to non-unique solutions. For example, it is impossible to uniquely reconstruct (with the above algoritm) target sequences which contain long stretches of a single base type within which a few bases of a different type are clustered. Thus, if 4-mer probes were used to reconstruct a sequence with a stretch containing —AAAAAAAAAAAAAAAAAAAAG-CATAAAAAAAAAAAAAAA— the position of GCAT within the sequence of A's cannot be unequivocally determined. In some cases, if alternative solutions are found the correct sequence can be discerned by sequencing the non-uniquely determined portions of the target sequence by standard techniques.

Different algorithms can be employed, and may be required for different embodiments of the invention. For example, it is clear from the general description of the reconstruction problem that it is amenable to solution on computers with parallel processing capabilities.

EXAMPLES

The following examples serve to illustrate the present invention. The concentrations of reagents, temperatures, probe lengths, labeling means, anchoring means, particular probe sets chosen, the algorithm used for reconstruction, and the values of other variable parameters are only to exemplify the invention and are not to be considered limitations thereof.

Example I. Sequence Determination of the 119 Basepair Sca-Xmn Fragment of pUC19 with 8-mer Probes A 119 basepair double stranded DNA is obtained by Xmn I and Sca I restriction endonuclease digestion of the pUC19 plasmid, described by Yanisch-Perron et al, Gene, Vol. 33, pgs. 103-119 (1985), and widely available commercially, e.g. Bethesda Research Laboratories (Gaithersburg, Md.). Large scale isolation of pUC19 can be carried out by standard procedures, e.g. as disclosed by Maniatis et al, *Molecular Cloning: A Laboratory Manual*, (Cold Spring Harbor Laboratory, N.Y., 1982) (i.e. alkali lysis followed by equilibrium centrifugation in cesium chloride-ethidium bromide gradient). Alternatively, purified pUC19 is purchased commercially as needed, e.g. from Bethesda Research Laboratories.

1 mg pUC19 DNA is precipitated with 95% ethanol, dried, and resuspended in 1 ml of Sca-Xmn restriction buffer (e.g., 50 mM NaCl, 10 mM Tris-HCl (pH 7.8), 10 mM $MgCl_2$, 10mM 2-mercaptoethanol, 100 ug bovine serum albumin) for about 2.0 hours at 37° C.

After stopping the reaction by adding 0.5 M EDTA (pH 7.5), the restriction buffer is mixed with xylene cyanol and loaded onto a 8 percent polyacrylamide gel for electrophoresis. The band containing the 119 basepair fragment is excised, and the DNA eluted as described by Maniatis et al, page 178 (cited above).

The fragments are resuspended at 1 ng/100 ul of 0.2 N NaOH for 10 minutes, chilled, and mixed with an equal volume of 10xSSC (1.5 M sodium chloride and 0.15 M sodium citrate). 100 ul samples of this fragment solution are pipetted into the wells of slot-blotting apparatus, e.g. eleven 72-well Minifold II micro-sample filtration manifolds, available from Schleicher and Scheull, Keene, N.H.), each apparatus holding a GeneScreen membrane that had been previously wetted for 15-20 minutes in 1xSSC. After 2 hours, the solution is gently sucked through the membranes, washed with 2xSSC, and allowed to dry. After drying, the membranes are baked at 80° C. for 2-4 hours. Before application of probe, the membranes are treated with prehybridization mixture (10x Denhardt's with 0.5% SDS for 1 hour at 60°]C., followed by washing with 2xSSC).

An alternative method for preparing the target sequences is to prepare two samples of the cloning vector: one carrying the target sequence and one without the target sequence. The vector with the target sequence is digested at only one of the insertion sites of the target sequence, denatured, and applied to a solid phase support. The vector without the target sequence is digested at the same site, denatured, and used to block the non-target sequences of the previously anchored DNA. Finally, probes are applied. For example, 1 mg of pUC19 is separated into two portions, A and B. Portion A is digested with Sca I, denatured in 0.2 N NaOH as described above, applied to the eleven 72-well Minifold II filtration manifolds as described above, washed, dried, and baked at 80° C. for 2-4 hours. Portion B is digested with both Sca I and Xmn I, the large fragment is isolated, e.g. by electrophoresis, by RPC-5 chromatography, or the like, concentrated by precipitation in ethanol, and resuspended, denatured (0.2 N NaOH at 37° C. for 30 min., neutralized with HCl, and brought to 6xSSC at 0° C.), mixed with hybridization solution (the resulting mixture being 5x Denhardt's, 5xSSPE (1xSSPE consisting of 180 mM NaCl, 10 mM ($Na_{1.5}$)$PO_4$, 1 mM $Na_2EDTA$, pH 8.0), and 0.5% SDS), and applied to the manifold membranes after they had been treated with prehybridization mixture (10x Denhardt's, with 0.5% SDS, for 1 hour at 60° C., followed by washing with 2xSSC).

Probes for hybridization are synthesized by phosphoramidite chemistry on an Applied Biosystems, Inc. model 380A DNA synthesizer. 4×196=784 mixed oligonucleotide probes are employed, a probe for each kind of 8-mer sequence having either a fixed initial position or a fixed final position (see Appendix I). Non-fixed positions of the cytosine and adenosine subsets of probes are filled by deoxyadenosine and deoxyinosine and deoxycytosine and deoxyinosine, respectively. The probes are $^{32}P$ labelled following the T4 polynucleotide kinase protocol of Maxum and Gilbert (*Meth Enzymol.*, Vol. 65, pgs. 497-560 (1980)), applied to the manifold wells at 18° C. for 16 hours at a concentration of 1 ng/ml in 500 ul of hybridization mixture consisting of 5x Denhardt's, 5xSSPE, and 0.5% SDS. After hybridization the membranes are washed 3 times with 6xSSC containing 0.5% SDS at 12° C., followed by 2 rinses with 3.0 M Me4NCl, 50 mM Tris-HCl (pH 8.0), 0.5% SDS at 12° C., and a final 2.0 minute wash in 3.0 M Me4NCl, 50 mM Tris-HCl (pH 8.0), 0.5% SDS at 26-27°. After washing, the dried membranes are autoradiographed on XAR-5 film (or its equivalent) for 2-4 days. "Slots" on the developed film are analyzed on a LKB UltroScan XL Laser Densitometer, or like instrument.

Numbers of perfectly matched probes are determined by comparing the relative signal strengths of probes having the same degree of degeneracy. Also, because a double stranded target sequence is used, the values for probe number used in the reconstruction algorithm are the average of the signal for each probe type and its complement (with respect to the fixed bases). The sequence is reconstructed from the probe number data by program RCON8, whose source code is listed in the Appendix RCON8 assumes that the eight base sequences on each end of the target sequence are known sequence regions. The program returns the noncoding sequence listed in a 3'-5' orientation from left to right.

EXAMPLE II. SEQUENCE DETERMINATION OF THE 323

BASEPAIR PVU II FRAGMENT OF PUC19

USING 9-MER PROBES

A 323 basepair double stranded DNA is one of two fragments obtained by Pvu II digestion of pUC19. The same procedure is followed as described in Example I for preparing the 323 basepair Pvu II fragments, denaturing them, and anchoring them to GeneScreen substrates. Pre-hybridization, hybridization, and wash protocols are the same, except that the final high temperature wash is carried out at 28–29° C.

Probes are synthesized and labeled as in Example I. 1556 probes are employed. A probe is prepared for each 9-mer sequence having a fixed base at the initial or final position (i.e. 389 each for A, C, G, and T probes). As in Example I, probes of the form 100000000 and 000000001 are replaced by three probes having different types of fixed bases, e.g. 00000000T is replaced by A0000000T, C0000000T, and G0000000T.

The sequence of the Pvu fragment is reconstructed with a modified version of the program of Appendix II which specifically accommodates 9-mer probe data. Like the 8-mer version, the program assumes that the nine base sequences on each end of the target sequence are known sequence regions.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

Appendix I. List of 8-mer Probes Used in Example I

The following list gives the different permutations of fixed bases (represented by letters) and non-fixed bases (represented by 0's) for the four subsets of mixed oligonucleotide probes. The numbering of the individual permutations corresponds to the indices of the various arrays in the program listed in Appendix II.

```
 1    A 0 0 0 0 0 0 C    C 0 0 0 0 0 0 A    G 0 0 0 0 0 0 A    T 0 0 0 0 0 0 A
 2    A 0 0 0 0 0 0 G    C 0 0 0 0 0 0 G    G 0 0 0 0 0 0 C    T 0 0 0 0 0 0 C
 3    A 0 0 0 0 0 0 T    C 0 0 0 0 0 0 T    G 0 0 0 0 0 0 T    T 0 0 0 0 0 0 G
 4    A A 0 0 0 0 0 0    C C 0 0 0 0 0 0    G G 0 0 0 0 0 0    T T 0 0 0 0 0 0
 5    A 0 A 0 0 0 0 0    C 0 C 0 0 0 0 0    G 0 G 0 0 0 0 0    T 0 T 0 0 0 0 0
 6    A 0 0 A 0 0 0 0    C 0 0 C 0 0 0 0    G 0 0 G 0 0 0 0    T 0 0 T 0 0 0 0
 7    A 0 0 0 A 0 0 0    C 0 0 0 C 0 0 0    G 0 0 0 G 0 0 0    T 0 0 0 T 0 0 0
 8    A 0 0 0 0 A 0 0    C 0 0 0 0 C 0 0    G 0 0 0 0 G 0 0    T 0 0 0 0 T 0 0
 9    A 0 0 0 0 0 A 0    C 0 0 0 0 0 C 0    G 0 0 0 0 0 G 0    T 0 0 0 0 0 T 0
10    A 0 0 0 0 0 0 A    C 0 0 0 0 0 0 C    G 0 0 0 0 0 0 G    T 0 0 0 0 0 0 T
11    A A A 0 0 0 0 0    C C C 0 0 0 0 0    G G G 0 0 0 0 0    T T T 0 0 0 0 0
12    A A 0 A 0 0 0 0    C C 0 C 0 0 0 0    G G 0 G 0 0 0 0    T T 0 T 0 0 0 0
13    A 0 A A 0 0 0 0    C 0 C C 0 0 0 0    G 0 G G 0 0 0 0    T 0 T T 0 0 0 0
14    A A 0 0 A 0 0 0    C C 0 0 C 0 0 0    G G 0 0 G 0 0 0    T T 0 0 T 0 0 0
15    A 0 A 0 A 0 0 0    C 0 C 0 C 0 0 0    G 0 G 0 G 0 0 0    T 0 T 0 T 0 0 0
16    A 0 0 A A 0 0 0    C 0 0 C C 0 0 0    G 0 0 G G 0 0 0    T 0 0 T T 0 0 0
17    A A 0 0 0 A 0 0    C C 0 0 0 C 0 0    G G 0 0 0 G 0 0    T T 0 0 0 T 0 0
18    A 0 A 0 0 A 0 0    C 0 C 0 0 C 0 0    G 0 G 0 0 G 0 0    T 0 T 0 0 T 0 0
19    A 0 0 A 0 A 0 0    C 0 0 C 0 C 0 0    G 0 0 G 0 G 0 0    T 0 0 T 0 T 0 0
20    A 0 0 0 A A 0 0    C 0 0 0 C C 0 0    G 0 0 0 G G 0 0    T 0 0 0 T T 0 0
21    A A 0 0 0 0 A 0    C C 0 0 0 0 C 0    G G 0 0 0 0 G 0    T T 0 0 0 0 T 0
22    A 0 A 0 0 0 A 0    C 0 C 0 0 0 C 0    G 0 G 0 0 0 G 0    T 0 T 0 0 0 T 0
23    A 0 0 A 0 0 A 0    C 0 0 C 0 0 C 0    G 0 0 G 0 0 G 0    T 0 0 T 0 0 T 0
24    A 0 0 0 A 0 A 0    C 0 0 0 C 0 C 0    G 0 0 0 G 0 G 0    T 0 0 0 T 0 T 0
25    A 0 0 0 0 A A 0    C 0 0 0 0 C C 0    G 0 0 0 0 G G 0    T 0 0 0 0 T T 0
26    A A 0 0 0 0 0 A    C C 0 0 0 0 0 C    G G 0 0 0 0 0 G    T T 0 0 0 0 0 T
27    A 0 A 0 0 0 0 A    C 0 C 0 0 0 0 C    G 0 G 0 0 0 0 G    T 0 T 0 0 0 0 T
28    A 0 0 A 0 0 0 A    C 0 0 C 0 0 0 C    G 0 0 G 0 0 0 G    T 0 0 T 0 0 0 T
29    A 0 0 0 A 0 0 A    C 0 0 0 C 0 0 C    G 0 0 0 G 0 0 G    T 0 0 0 T 0 0 T
30    A 0 0 0 0 A 0 A    C 0 0 0 0 C 0 C    G 0 0 0 0 G 0 G    T 0 0 0 0 T 0 T
31    A 0 0 0 0 0 A A    C 0 0 0 0 0 C C    G 0 0 0 0 0 G G    T 0 0 0 0 0 T T
32    A A A A 0 0 0 0    C C C C 0 0 0 0    G G G G 0 0 0 0    T T T T 0 0 0 0
33    A A A 0 A 0 0 0    C C C 0 C 0 0 0    G G G 0 G 0 0 0    T T T 0 T 0 0 0
34    A A 0 A A 0 0 0    C C 0 C C 0 0 0    G G 0 G G 0 0 0    T T 0 T T 0 0 0
35    A 0 A A A 0 0 0    C 0 C C C 0 0 0    G 0 G G G 0 0 0    T 0 T T T 0 0 0
36    A A A 0 0 A 0 0    C C C 0 0 C 0 0    G G G 0 0 G 0 0    T T T 0 0 T 0 0
37    A A 0 A 0 A 0 0    C C 0 C 0 C 0 0    G G 0 G 0 G 0 0    T T 0 T 0 T 0 0
```

```
38   A 0 A A 0 A 0 0    C 0 C C 0 C 0 0    G 0 G G 0 G 0 0    T 0 T T 0 T 0 0
39   A A 0 0 A A 0 0    C C 0 0 C C 0 0    G G 0 0 G G 0 0    T T 0 0 T T 0 0
40   A 0 A 0 A A 0 0    C 0 C 0 C C 0 0    G 0 G 0 G G 0 0    T 0 T 0 T T 0 0
41   A 0 0 A A A 0 0    C 0 0 C C C 0 0    G 0 0 G G G 0 0    T 0 0 T T T 0 0
42   A A A 0 0 0 A 0    C C C 0 0 0 C 0    G G G 0 0 0 G 0    T T T 0 0 0 T 0
43   A A 0 A 0 0 A 0    C C 0 C 0 0 C 0    G G 0 G 0 0 G 0    T T 0 T 0 0 T 0
44   A 0 A A 0 0 A 0    C 0 C C 0 0 C 0    G 0 G G 0 0 G 0    T 0 T T 0 0 T 0
45   A A 0 0 A 0 A 0    C C 0 0 C 0 C 0    G G 0 0 G 0 G 0    T T 0 0 T 0 T 0
46   A 0 A 0 A 0 A 0    C 0 C 0 C 0 C 0    G 0 G 0 G 0 G 0    T 0 T 0 T 0 T 0
47   A 0 0 A A 0 A 0    C 0 0 C C 0 C 0    G 0 0 G G 0 G 0    T 0 0 T T 0 T 0
48   A A 0 0 0 A A 0    C C 0 0 0 C C 0    G G 0 0 0 G G 0    T T 0 0 0 T T 0
49   A 0 A 0 0 A A 0    C 0 C 0 0 C C 0    G 0 G 0 0 G G 0    T 0 T 0 0 T T 0
50   A 0 0 A 0 A A 0    C 0 0 C 0 C C 0    G 0 0 G 0 G G 0    T 0 0 T 0 T T 0
51   A 0 0 0 A A A 0    C 0 0 0 C C C 0    G 0 0 0 G G G 0    T 0 0 0 T T T 0
52   A A A 0 0 0 0 A    C C C 0 0 0 0 C    G G G 0 0 0 0 G    T T T 0 0 0 0 T
53   A A 0 A 0 0 0 A    C C 0 C 0 0 0 C    G G 0 G 0 0 0 G    T T 0 T 0 0 0 T
54   A 0 A A 0 0 0 A    C 0 C C 0 0 0 C    G 0 G G 0 0 0 G    T 0 T T 0 0 0 T
55   A A 0 0 A 0 0 A    C C 0 0 C 0 0 C    G G 0 0 G 0 0 G    T T 0 0 T 0 0 T
56   A 0 A 0 A 0 0 A    C 0 C 0 C 0 0 C    G 0 G 0 G 0 0 G    T 0 T 0 T 0 0 T
57   A 0 0 A A 0 0 A    C 0 0 C C 0 0 C    G 0 0 G G 0 0 G    T 0 0 T T 0 0 T
58   A A 0 0 0 A 0 A    C C 0 0 0 C 0 C    G G 0 0 0 G 0 G    T T 0 0 0 T 0 T
59   A 0 A 0 0 A 0 A    C 0 C 0 0 C 0 C    G 0 G 0 0 G 0 G    T 0 T 0 0 T 0 T
60   A 0 0 A 0 A 0 A    C 0 0 C 0 C 0 C    G 0 0 G 0 G 0 G    T 0 0 T 0 T 0 T
61   A 0 0 0 A A 0 A    C 0 0 0 C C 0 C    G 0 0 0 G G 0 G    T 0 0 0 T T 0 T
62   A A 0 0 0 0 A A    C C 0 0 0 0 C C    G G 0 0 0 0 G G    T T 0 0 0 0 T T
63   A 0 A 0 0 0 A A    C 0 C 0 0 0 C C    G 0 G 0 0 0 G G    T 0 T 0 0 0 T T
64   A 0 0 A 0 0 A A    C 0 0 C 0 0 C C    G 0 0 G 0 0 G G    T 0 0 T 0 0 T T
65   A 0 0 0 A 0 A A    C 0 0 0 C 0 C C    G 0 0 0 G 0 G G    T 0 0 0 T 0 T T
66   A 0 0 0 0 A A A    C 0 0 0 0 C C C    G 0 0 0 0 G G G    T 0 0 0 0 T T T
67   A A A A A 0 0 0    C C C C C 0 0 0    G G G G G 0 0 0    T T T T T 0 0 0
68   A A A A 0 A 0 0    C C C C 0 C 0 0    G G G G 0 G 0 0    T T T T 0 T 0 0
69   A A A 0 A A 0 0    C C C 0 C C 0 0    G G G 0 G G 0 0    T T T 0 T T 0 0
70   A A 0 A A A 0 0    C C 0 C C C 0 0    G G 0 G G G 0 0    T T 0 T T T 0 0
71   A 0 A A A A 0 0    C 0 C C C C 0 0    G 0 G G G G 0 0    T 0 T T T T 0 0
72   A A A A 0 0 A 0    C C C C 0 0 C 0    G G G G 0 0 G 0    T T T T 0 0 T 0
73   A A A 0 A 0 A 0    C C C 0 C 0 C 0    G G G 0 G 0 G 0    T T T 0 T 0 T 0
74   A A 0 A A 0 A 0    C C 0 C C 0 C 0    G G 0 G G 0 G 0    T T 0 T T 0 T 0
75   A 0 A A A 0 A 0    C 0 C C C 0 C 0    G 0 G G G 0 G 0    T 0 T T T 0 T 0
76   A A A 0 0 A A 0    C C C 0 0 C C 0    G G G 0 0 G G 0    T T T 0 0 T T 0
77   A A 0 A 0 A A 0    C C 0 C 0 C C 0    G G 0 G 0 G G 0    T T 0 T 0 T T 0
78   A 0 A A 0 A A 0    C 0 C C 0 C C 0    G 0 G G 0 G G 0    T 0 T T 0 T T 0
79   A A 0 0 A A A 0    C C 0 0 C C C 0    G G 0 0 G G G 0    T T 0 0 T T T 0
80   A 0 A 0 A A A 0    C 0 C 0 C C C 0    G 0 G 0 G G G 0    T 0 T 0 T T T 0
81   A 0 0 A A A A 0    C 0 0 C C C C 0    G 0 0 G G G G 0    T 0 0 T T T T 0
82   A A A A 0 0 0 A    C C C C 0 0 0 C    G G G G 0 0 0 G    T T T T 0 0 0 T
83   A A A 0 A 0 0 A    C C C 0 C 0 0 C    G G G 0 G 0 0 G    T T T 0 T 0 0 T
84   A A 0 A A 0 0 A    C C 0 C C 0 0 C    G G 0 G G 0 0 G    T T 0 T T 0 0 T
85   A 0 A A A 0 0 A    C 0 C C C 0 0 C    G 0 G G G 0 0 G    T 0 T T T 0 0 T
86   A A A 0 0 A 0 A    C C C 0 0 C 0 C    G G G 0 0 G 0 G    T T T 0 0 T 0 T
87   A A 0 A 0 A 0 A    C C 0 C 0 C 0 C    G G 0 G 0 G 0 G    T T 0 T 0 T 0 T
88   A 0 A A 0 A 0 A    C 0 C C 0 C 0 C    G 0 G G 0 G 0 G    T 0 T T 0 T 0 T
89   A A 0 0 A A 0 A    C C 0 0 C C 0 C    G G 0 0 G G 0 G    T T 0 0 T T 0 T
90   A 0 A 0 A A 0 A    C 0 C 0 C C 0 C    G 0 G 0 G G 0 G    T 0 T 0 T T 0 T
91   A 0 0 A A A 0 A    C 0 0 C C C 0 C    G 0 0 G G G 0 G    T 0 0 T T T 0 T
92   A A A 0 0 0 A A    C C C 0 0 0 C C    G G G 0 0 0 G G    T T T 0 0 0 T T
93   A A 0 A 0 0 A A    C C 0 C 0 0 C C    G G 0 G 0 0 G G    T T 0 T 0 0 T T
94   A 0 A A 0 0 A A    C 0 C C 0 0 C C    G 0 G G 0 0 G G    T 0 T T 0 0 T T
```

```
 95  A A 0 0 A 0 A A    C C 0 0 C 0 C C    G G 0 0 G 0 G G    T T 0 0 T 0 T T
 96  A 0 A 0 A 0 A A    C 0 C 0 C 0 C C    G 0 G 0 G 0 G G    T 0 T 0 T 0 T T
 97  A 0 0 A A 0 A A    C 0 0 C C 0 C C    G 0 0 G G 0 G G    T 0 0 T T 0 T T
 98  A A 0 0 0 A A A    C C 0 0 0 C C C    G G 0 0 0 G G G    T T 0 0 0 T T T
 99  A 0 A 0 0 A A A    C 0 C 0 0 C C C    G 0 G 0 0 G G G    T 0 T 0 0 T T T
100  A 0 0 A 0 A A A    C 0 0 C 0 C C C    G 0 0 G 0 G G G    T 0 0 T 0 T T T
101  A 0 0 0 A A A A    C 0 0 0 C C C C    G 0 0 0 G G G G    T 0 0 0 T T T T
102  A A A A A A 0 0    C C C C C C 0 0    G G G G G G 0 0    T T T T T T 0 0
103  A A A A A 0 A 0    C C C C C 0 C 0    G G G G G 0 G 0    T T T T T 0 T 0
104  A A A A 0 A A 0    C C C C 0 C C 0    G G G G 0 G G 0    T T T T 0 T T 0
105  A A A 0 A A A 0    C C C 0 C C C 0    G G G 0 G G G 0    T T T 0 T T T 0
106  A A 0 A A A A 0    C C 0 C C C C 0    G G 0 G G G G 0    T T 0 T T T T 0
107  A 0 A A A A A 0    C 0 C C C C C 0    G 0 G G G G G 0    T 0 T T T T T 0
108  A A A A A 0 0 A    C C C C C 0 0 C    G G G G G 0 0 G    T T T T T 0 0 T
109  A A A A 0 A 0 A    C C C C 0 C 0 C    G G G G 0 G 0 G    T T T T 0 T 0 T
110  A A A 0 A A 0 A    C C C 0 C C 0 C    G G G 0 G G 0 G    T T T 0 T T 0 T
111  A A 0 A A A 0 A    C C 0 C C C 0 C    G G 0 G G G 0 G    T T 0 T T T 0 T
112  A 0 A A A A 0 A    C 0 C C C C 0 C    G 0 G G G G 0 G    T 0 T T T T 0 T
113  A A A A 0 0 A A    C C C C 0 0 C C    G G G G 0 0 G G    T T T T 0 0 T T
114  A A A 0 A 0 A A    C C C 0 C 0 C C    G G G 0 G 0 G G    T T T 0 T 0 T T
115  A A 0 A A 0 A A    C C 0 C C 0 C C    G G 0 G G 0 G G    T T 0 T T 0 T T
116  A 0 A A A 0 A A    C 0 C C C 0 C C    G 0 G G G 0 G G    T 0 T T T 0 T T
117  A A A 0 0 A A A    C C C 0 0 C C C    G G G 0 0 G G G    T T T 0 0 T T T
118  A A 0 A 0 A A A    C C 0 C 0 C C C    G G 0 G 0 G G G    T T 0 T 0 T T T
119  A 0 A A 0 A A A    C 0 C C 0 C C C    G 0 G G 0 G G G    T 0 T T 0 T T T
120  A A 0 0 A A A A    C C 0 0 C C C C    G G 0 0 G G G G    T T 0 0 T T T T
121  A 0 A 0 A A A A    C 0 C 0 C C C C    G 0 G 0 G G G G    T 0 T 0 T T T T
122  A 0 0 A A A A A    C 0 0 C C C C C    G 0 0 G G G G G    T 0 0 T T T T T
123  A A A A A A A 0    C C C C C C C 0    G G G G G G G 0    T T T T T T T 0
124  A A A A A A 0 A    C C C C C C 0 C    G G G G G G 0 G    T T T T T T 0 T
125  A A A A A 0 A A    C C C C C 0 C C    G G G G G 0 G G    T T T T T 0 T T
126  A A A A 0 A A A    C C C C 0 C C C    G G G G 0 G G G    T T T T 0 T T T
127  A A A 0 A A A A    C C C 0 C C C C    G G G 0 G G G G    T T T 0 T T T T
128  A A 0 A A A A A    C C 0 C C C C C    G G 0 G G G G G    T T 0 T T T T T
129  A 0 A A A A A A    C 0 C C C C C C    G 0 G G G G G G    T 0 T T T T T T
130  A A A A A A A A    C C C C C C C C    G G G G G G G G    T T T T T T T T
131  0 A 0 0 0 0 0 0    0 C 0 0 0 0 0 0    0 G 0 0 0 0 0 0    0 T 0 0 0 0 0 0
132  0 0 A 0 0 0 0 0    0 0 C 0 0 0 0 0    0 0 G 0 0 0 0 0    0 0 T 0 0 0 0 0
133  0 0 0 A 0 0 0 0    0 0 0 C 0 0 0 0    0 0 0 G 0 0 0 0    0 0 0 T 0 0 0 0
134  0 0 0 0 A 0 0 0    0 0 0 0 C 0 0 0    0 0 0 0 G 0 0 0    0 0 0 0 T 0 0 0
135  0 0 0 0 0 A 0 0    0 0 0 0 0 C 0 0    0 0 0 0 0 G 0 0    0 0 0 0 0 T 0 0
136  0 0 0 0 0 0 A 0    0 0 0 0 0 0 C 0    0 0 0 0 0 0 G 0    0 0 0 0 0 0 T 0
137  C 0 0 0 0 0 0 A    A 0 0 0 0 0 0 C    A 0 0 0 0 0 0 G    A 0 0 0 0 0 0 T
138  G 0 0 0 0 0 0 A    G 0 0 0 0 0 0 C    C 0 0 0 0 0 0 G    C 0 0 0 0 0 0 T
139  T 0 0 0 0 0 0 A    T 0 0 0 0 0 0 C    T 0 0 0 0 0 0 G    G 0 0 0 0 0 0 T
140  0 A A 0 0 0 0 0    0 C C 0 0 0 0 0    0 G G 0 0 0 0 0    0 T T 0 0 0 0 0
141  0 A 0 A 0 0 0 0    0 C 0 C 0 0 0 0    0 G 0 G 0 0 0 0    0 T 0 T 0 0 0 0
142  0 0 A A 0 0 0 0    0 0 C C 0 0 0 0    0 0 G G 0 0 0 0    0 0 T T 0 0 0 0
143  0 A 0 0 A 0 0 0    0 C 0 0 C 0 0 0    0 G 0 0 G 0 0 0    0 T 0 0 T 0 0 0
144  0 0 A 0 A 0 0 0    0 0 C 0 C 0 0 0    0 0 G 0 G 0 0 0    0 0 T 0 T 0 0 0
145  0 0 0 A A 0 0 0    0 0 0 C C 0 0 0    0 0 0 G G 0 0 0    0 0 0 T T 0 0 0
146  0 A 0 0 0 A 0 0    0 C 0 0 0 C 0 0    0 G 0 0 0 G 0 0    0 T 0 0 0 T 0 0
147  0 0 A 0 0 A 0 0    0 0 C 0 0 C 0 0    0 0 G 0 0 G 0 0    0 0 T 0 0 T 0 0
148  0 0 0 A 0 A 0 0    0 0 0 C 0 C 0 0    0 0 0 G 0 G 0 0    0 0 0 T 0 T 0 0
149  0 0 0 0 A A 0 0    0 0 0 0 C C 0 0    0 0 0 0 G G 0 0    0 0 0 0 T T 0 0
150  0 A 0 0 0 0 A 0    0 C 0 0 0 0 C 0    0 G 0 0 0 0 G 0    0 T 0 0 0 0 T 0
```

| | | | | |
|---|---|---|---|---|
| 151 | 0 0 A 0 0 0 A 0 | 0 0 C 0 0 0 C 0 | 0 0 G 0 0 0 G 0 | 0 0 T 0 0 0 T 0 |
| 152 | 0 0 0 A 0 0 A 0 | 0 0 0 C 0 0 C 0 | 0 0 0 G 0 0 G 0 | 0 0 0 T 0 0 T 0 |
| 153 | 0 0 0 0 A 0 A 0 | 0 0 0 0 C 0 C 0 | 0 0 0 0 G 0 G 0 | 0 0 0 0 T 0 T 0 |
| 154 | 0 0 0 0 0 A A 0 | 0 0 0 0 0 C C 0 | 0 0 0 0 0 G G 0 | 0 0 0 0 0 T T 0 |
| 155 | 0 A 0 0 0 0 0 A | 0 C 0 0 0 0 0 C | 0 G 0 0 0 0 0 G | 0 T 0 0 0 0 0 T |
| 156 | 0 0 A 0 0 0 0 A | 0 0 C 0 0 0 0 C | 0 0 G 0 0 0 0 G | 0 0 T 0 0 0 0 T |
| 157 | 0 0 0 A 0 0 0 A | 0 0 0 C 0 0 0 C | 0 0 0 G 0 0 0 G | 0 0 0 T 0 0 0 T |
| 158 | 0 0 0 0 A 0 0 A | 0 0 0 0 C 0 0 C | 0 0 0 0 G 0 0 G | 0 0 0 0 T 0 0 T |
| 159 | 0 0 0 0 0 A 0 A | 0 0 0 0 0 C 0 C | 0 0 0 0 0 G 0 G | 0 0 0 0 0 T 0 T |
| 160 | 0 0 0 0 0 0 A A | 0 0 0 0 0 0 C C | 0 0 0 0 0 0 G G | 0 0 0 0 0 0 T T |
| 161 | 0 A A A 0 0 0 0 | 0 C C C 0 0 0 0 | 0 G G G 0 0 0 0 | 0 T T T 0 0 0 0 |
| 162 | 0 A A 0 A 0 0 0 | 0 C C 0 C 0 0 0 | 0 G G 0 G 0 0 0 | 0 T T 0 T 0 0 0 |
| 163 | 0 A 0 A A 0 0 0 | 0 C 0 C C 0 0 0 | 0 G 0 G G 0 0 0 | 0 T 0 T T 0 0 0 |
| 164 | 0 0 A A A 0 0 0 | 0 0 C C C 0 0 0 | 0 0 G G G 0 0 0 | 0 0 T T T 0 0 0 |
| 165 | 0 A A 0 0 A 0 0 | 0 C C 0 0 C 0 0 | 0 G G 0 0 G 0 0 | 0 T T 0 0 T 0 0 |
| 166 | 0 A 0 A 0 A 0 0 | 0 C 0 C 0 C 0 0 | 0 G 0 G 0 G 0 0 | 0 T 0 T 0 T 0 0 |
| 167 | 0 0 A A 0 A 0 0 | 0 0 C C 0 C 0 0 | 0 0 G G 0 G 0 0 | 0 0 T T 0 T 0 0 |
| 168 | 0 A 0 0 A A 0 0 | 0 C 0 0 C C 0 0 | 0 G 0 0 G G 0 0 | 0 T 0 0 T T 0 0 |
| 169 | 0 0 A 0 A A 0 0 | 0 0 C 0 C C 0 0 | 0 0 G 0 G G 0 0 | 0 0 T 0 T T 0 0 |
| 170 | 0 0 0 A A A 0 0 | 0 0 0 C C C 0 0 | 0 0 0 G G G 0 0 | 0 0 0 T T T 0 0 |
| 171 | 0 A A 0 0 0 A 0 | 0 C C 0 0 0 C 0 | 0 G G 0 0 0 G 0 | 0 T T 0 0 0 T 0 |
| 172 | 0 A 0 A 0 0 A 0 | 0 C 0 C 0 0 C 0 | 0 G 0 G 0 0 G 0 | 0 T 0 T 0 0 T 0 |
| 173 | 0 0 A A 0 0 A 0 | 0 0 C C 0 0 C 0 | 0 0 G G 0 0 G 0 | 0 0 T T 0 0 T 0 |
| 174 | 0 A 0 0 A 0 A 0 | 0 C 0 0 C 0 C 0 | 0 G 0 0 G 0 G 0 | 0 T 0 0 T 0 T 0 |
| 175 | 0 0 A 0 A 0 A 0 | 0 0 C 0 C 0 C 0 | 0 0 G 0 G 0 G 0 | 0 0 T 0 T 0 T 0 |
| 176 | 0 0 0 A A 0 A 0 | 0 0 0 C C 0 C 0 | 0 0 0 G G 0 G 0 | 0 0 0 T T 0 T 0 |
| 177 | 0 A 0 0 0 A A 0 | 0 C 0 0 0 C C 0 | 0 G 0 0 0 G G 0 | 0 T 0 0 0 T T 0 |
| 178 | 0 0 A 0 0 A A 0 | 0 0 C 0 0 C C 0 | 0 0 G 0 0 G G 0 | 0 0 T 0 0 T T 0 |
| 179 | 0 0 0 A 0 A A 0 | 0 0 0 C 0 C C 0 | 0 0 0 G 0 G G 0 | 0 0 0 T 0 T T 0 |
| 180 | 0 0 0 0 A A A 0 | 0 0 0 0 C C C 0 | 0 0 0 0 G G G 0 | 0 0 0 0 T T T 0 |
| 181 | 0 A A 0 0 0 0 A | 0 C C 0 0 0 0 C | 0 G G 0 0 0 0 G | 0 T T 0 0 0 0 T |
| 182 | 0 A 0 A 0 0 0 A | 0 C 0 C 0 0 0 C | 0 G 0 G 0 0 0 G | 0 T 0 T 0 0 0 T |
| 183 | 0 0 A A 0 0 0 A | 0 0 C C 0 0 0 C | 0 0 G G 0 0 0 G | 0 0 T T 0 0 0 T |
| 184 | 0 A 0 0 A 0 0 A | 0 C 0 0 C 0 0 C | 0 G 0 0 G 0 0 G | 0 T 0 0 T 0 0 T |
| 185 | 0 0 A 0 A 0 0 A | 0 0 C 0 C 0 0 C | 0 0 G 0 G 0 0 G | 0 0 T 0 T 0 0 T |
| 186 | 0 0 0 A A 0 0 A | 0 0 0 C C 0 0 C | 0 0 0 G G 0 0 G | 0 0 0 T T 0 0 T |
| 187 | 0 A 0 0 0 A 0 A | 0 C 0 0 0 C 0 C | 0 G 0 0 0 G 0 G | 0 T 0 0 0 T 0 T |
| 188 | 0 0 A 0 0 A 0 A | 0 0 C 0 0 C 0 C | 0 0 G 0 0 G 0 G | 0 0 T 0 0 T 0 T |
| 189 | 0 0 0 A 0 A 0 A | 0 0 0 C 0 C 0 C | 0 0 0 G 0 G 0 G | 0 0 0 T 0 T 0 T |
| 190 | 0 0 0 0 A A 0 A | 0 0 0 0 C C 0 C | 0 0 0 0 G G 0 G | 0 0 0 0 T T 0 T |
| 191 | 0 A 0 0 0 0 A A | 0 C 0 0 0 0 C C | 0 G 0 0 0 0 G G | 0 T 0 0 0 0 T T |
| 192 | 0 0 A 0 0 0 A A | 0 0 C 0 0 0 C C | 0 0 G 0 0 0 G G | 0 0 T 0 0 0 T T |
| 193 | 0 0 0 A 0 0 A A | 0 0 0 C 0 0 C C | 0 0 0 G 0 0 G G | 0 0 0 T 0 0 T T |
| 194 | 0 0 0 0 A 0 A A | 0 0 0 0 C 0 C C | 0 0 0 0 G 0 G G | 0 0 0 0 T 0 T T |
| 195 | 0 0 0 0 0 A A A | 0 0 0 0 0 C C C | 0 0 0 0 0 G G G | 0 0 0 0 0 T T T |
| 196 | 0 A A A A 0 0 0 | 0 C C C C 0 0 0 | 0 G G G G 0 0 0 | 0 T T T T 0 0 0 |
| 197 | 0 A A A 0 A 0 0 | 0 C C C 0 C 0 0 | 0 G G G 0 G 0 0 | 0 T T T 0 T 0 0 |
| 198 | 0 A A 0 A A 0 0 | 0 C C 0 C C 0 0 | 0 G G 0 G G 0 0 | 0 T T 0 T T 0 0 |
| 199 | 0 A 0 A A A 0 0 | 0 C 0 C C C 0 0 | 0 G 0 G G G 0 0 | 0 T 0 T T T 0 0 |
| 200 | 0 0 A A A A 0 0 | 0 0 C C C C 0 0 | 0 0 G G G G 0 0 | 0 0 T T T T 0 0 |
| 201 | 0 A A A 0 0 A 0 | 0 C C C 0 0 C 0 | 0 G G G 0 0 G 0 | 0 T T T 0 0 T 0 |
| 202 | 0 A A 0 A 0 A 0 | 0 C C 0 C 0 C 0 | 0 G G 0 G 0 G 0 | 0 T T 0 T 0 T 0 |
| 203 | 0 A 0 A A 0 A 0 | 0 C 0 C C 0 C 0 | 0 G 0 G G 0 G 0 | 0 T 0 T T 0 T 0 |
| 204 | 0 0 A A A 0 A 0 | 0 0 C C C 0 C 0 | 0 0 G G G 0 G 0 | 0 0 T T T 0 T 0 |
| 205 | 0 A A 0 0 A A 0 | 0 C C 0 0 C C 0 | 0 G G 0 0 G G 0 | 0 T T 0 0 T T 0 |
| 206 | 0 A 0 A 0 A A 0 | 0 C 0 C 0 C C 0 | 0 G 0 G 0 G G 0 | 0 T 0 T 0 T T 0 |
| 207 | 0 0 A A 0 A A 0 | 0 0 C C 0 C C 0 | 0 0 G G 0 G G 0 | 0 0 T T 0 T T 0 |

| | | | | | | | |
|---|---|---|---|---|---|---|---|
| 208 | 0 A 0 0 A A A 0 | 0 C 0 0 C C C 0 | 0 G 0 0 G G G 0 | 0 T 0 0 T T T 0 |
| 209 | 0 0 A 0 A A A 0 | 0 0 C 0 C C C 0 | 0 0 G 0 G G G 0 | 0 0 T 0 T T T 0 |
| 210 | 0 0 0 A A A A 0 | 0 0 0 C C C C 0 | 0 0 0 G G G G 0 | 0 0 0 T T T T 0 |
| 211 | 0 A A A 0 0 0 A | 0 C C C 0 0 0 C | 0 G G G 0 0 0 G | 0 T T T 0 0 0 T |
| 212 | 0 A A 0 A 0 0 A | 0 C C 0 C 0 0 C | 0 G G 0 G 0 0 G | 0 T T 0 T 0 0 T |
| 213 | 0 A 0 A A 0 0 A | 0 C 0 C C 0 0 C | 0 G 0 G G 0 0 G | 0 T 0 T T 0 0 T |
| 214 | 0 0 A A A 0 0 A | 0 0 C C C 0 0 C | 0 0 G G G 0 0 G | 0 0 T T T 0 0 T |
| 215 | 0 A A 0 0 A 0 A | 0 C C 0 0 C 0 C | 0 G G 0 0 G 0 G | 0 T T 0 0 T 0 T |
| 216 | 0 A 0 A 0 A 0 A | 0 C 0 C 0 C 0 C | 0 G 0 G 0 G 0 G | 0 T 0 T 0 T 0 T |
| 217 | 0 0 A A 0 A 0 A | 0 0 C C 0 C 0 C | 0 0 G G 0 G 0 G | 0 0 T T 0 T 0 T |
| 218 | 0 A 0 0 A A 0 A | 0 C 0 0 C C 0 C | 0 G 0 0 G G 0 G | 0 T 0 0 T T 0 T |
| 219 | 0 0 A 0 A A 0 A | 0 0 C 0 C C 0 C | 0 0 G 0 G G 0 G | 0 0 T 0 T T 0 T |
| 220 | 0 0 0 A A A 0 A | 0 0 0 C C C 0 C | 0 0 0 G G G 0 G | 0 0 0 T T T 0 T |
| 221 | 0 A A 0 0 0 A A | 0 C C 0 0 0 C C | 0 G G 0 0 0 G G | 0 T T 0 0 0 T T |
| 222 | 0 A 0 A 0 0 A A | 0 C 0 C 0 0 C C | 0 G 0 G 0 0 G G | 0 T 0 T 0 0 T T |
| 223 | 0 0 A A 0 0 A A | 0 0 C C 0 0 C C | 0 0 G G 0 0 G G | 0 0 T T 0 0 T T |
| 224 | 0 A 0 0 A 0 A A | 0 C 0 0 C 0 C C | 0 G 0 0 G 0 G G | 0 T 0 0 T 0 T T |
| 225 | 0 0 A 0 A 0 A A | 0 0 C 0 C 0 C C | 0 0 G 0 G 0 G G | 0 0 T 0 T 0 T T |
| 226 | 0 0 0 A A 0 A A | 0 0 0 C C 0 C C | 0 0 0 G G 0 G G | 0 0 0 T T 0 T T |
| 227 | 0 A 0 0 0 A A A | 0 C 0 0 0 C C C | 0 G 0 0 0 G G G | 0 T 0 0 0 T T T |
| 228 | 0 0 A 0 0 A A A | 0 0 C 0 0 C C C | 0 0 G 0 0 G G G | 0 0 T 0 0 T T T |
| 229 | 0 0 0 A 0 A A A | 0 0 0 C 0 C C C | 0 0 0 G 0 G G G | 0 0 0 T 0 T T T |
| 230 | 0 0 0 0 A A A A | 0 0 0 0 C C C C | 0 0 0 0 G G G G | 0 0 0 0 T T T T |
| 231 | 0 A A A A A 0 0 | 0 C C C C C 0 0 | 0 G G G G G 0 0 | 0 T T T T T 0 0 |
| 232 | 0 A A A A 0 A 0 | 0 C C C C 0 C 0 | 0 G G G G 0 G 0 | 0 T T T T 0 T 0 |
| 233 | 0 A A A 0 A A 0 | 0 C C C 0 C C 0 | 0 G G G 0 G G 0 | 0 T T T 0 T T 0 |
| 234 | 0 A A 0 A A A 0 | 0 C C 0 C C C 0 | 0 G G 0 G G G 0 | 0 T T 0 T T T 0 |
| 235 | 0 A 0 A A A A 0 | 0 C 0 C C C C 0 | 0 G 0 G G G G 0 | 0 T 0 T T T T 0 |
| 236 | 0 0 A A A A A 0 | 0 0 C C C C C 0 | 0 0 G G G G G 0 | 0 0 T T T T T 0 |
| 237 | 0 A A A A 0 0 A | 0 C C C C 0 0 C | 0 G G G G 0 0 G | 0 T T T T 0 0 T |
| 238 | 0 A A A 0 A 0 A | 0 C C C 0 C 0 C | 0 G G G 0 G 0 G | 0 T T T 0 T 0 T |
| 239 | 0 A A 0 A A 0 A | 0 C C 0 C C 0 C | 0 G G 0 G G 0 G | 0 T T 0 T T 0 T |
| 240 | 0 A 0 A A A 0 A | 0 C 0 C C C 0 C | 0 G 0 G G G 0 G | 0 T 0 T T T 0 T |
| 241 | 0 0 A A A A 0 A | 0 0 C C C C 0 C | 0 0 G G G G 0 G | 0 0 T T T T 0 T |
| 242 | 0 A A A 0 0 A A | 0 C C C 0 0 C C | 0 G G G 0 0 G G | 0 T T T 0 0 T T |
| 243 | 0 A A 0 A 0 A A | 0 C C 0 C 0 C C | 0 G G 0 G 0 G G | 0 T T 0 T 0 T T |
| 244 | 0 A 0 A A 0 A A | 0 C 0 C C 0 C C | 0 G 0 G G 0 G G | 0 T 0 T T 0 T T |
| 245 | 0 0 A A A 0 A A | 0 0 C C C 0 C C | 0 0 G G G 0 G G | 0 0 T T T 0 T T |
| 246 | 0 A A 0 0 A A A | 0 C C 0 0 C C C | 0 G G 0 0 G G G | 0 T T 0 0 T T T |
| 247 | 0 A 0 A 0 A A A | 0 C 0 C 0 C C C | 0 G 0 G 0 G G G | 0 T 0 T 0 T T T |
| 248 | 0 0 A A 0 A A A | 0 0 C C 0 C C C | 0 0 G G 0 G G G | 0 0 T T 0 T T T |
| 249 | 0 A 0 0 A A A A | 0 C 0 0 C C C C | 0 G 0 0 G G G G | 0 T 0 0 T T T T |
| 250 | 0 0 A 0 A A A A | 0 0 C 0 C C C C | 0 0 G 0 G G G G | 0 0 T 0 T T T T |
| 251 | 0 0 0 A A A A A | 0 0 0 C C C C C | 0 0 0 G G G G G | 0 0 0 T T T T T |
| 252 | 0 A A A A A A 0 | 0 C C C C C C 0 | 0 G G G G G G 0 | 0 T T T T T T 0 |
| 253 | 0 A A A A A 0 A | 0 C C C C C 0 C | 0 G G G G G 0 G | 0 T T T T T 0 T |
| 254 | 0 A A A A 0 A A | 0 C C C C 0 C C | 0 G G G G 0 G G | 0 T T T T 0 T T |
| 255 | 0 A A A 0 A A A | 0 C C C 0 C C C | 0 G G G 0 G G G | 0 T T T 0 T T T |
| 256 | 0 A A 0 A A A A | 0 C C 0 C C C C | 0 G G 0 G G G G | 0 T T 0 T T T T |
| 257 | 0 A 0 A A A A A | 0 C 0 C C C C C | 0 G 0 G G G G G | 0 T 0 T T T T T |
| 258 | 0 0 A A A A A A | 0 0 C C C C C C | 0 0 G G G G G G | 0 0 T T T T T T |
| 259 | 0 A A A A A A A | 0 C C C C C C C | 0 G G G G G G G | 0 T T T T T T T |

Appendix II. Source Code Listing of Reconstruction Algorithm RCON8

```fortran
1:          program RCON8
2: c
3: *c
4: c          Program RCON8 reconstructs sequences from 8-mer probes
5: c              having fixed bases at their initial positions
6: c              and fixed bases at their final positions.
7: c
8: c
9:          implicit integer*2 (a-z)
10:         dimension r1(9999,120),r2(9999,120),l1(9999,120),l2(9999,120)
11:         dimension dr2(9999,120),dl1(9999,120),dl2(9999,120),dr1num(9999)
12:         dimension dr2num(9999),dl1num(9999),dl2num(9999),pset(240,2)
13:         dimension pnum8(4,259,8),rreg1(9999,7),rreg2(9999,7)
14:         dimension lreg2(9999,7),lreg1(9999,7)
15:         dimension tab(4,-4:4),dr1(9999,120)
16:         dimension na(259),nc(259),ng(259),nt(259)
17:         character*1 seql(120),seqr(120),s,pseq8(4,259,8)
18: c
19:         character*10 pdata
20:         common r1,r2,l1,l2,dr1,dr2,dl1,dl2,rreg1,rreg2,lreg1,lreg2,
21:       1         pnum8,tab,dr1num,dr2num,dl1num,dl2num,npx,np0,pset,pseq8
22: c
23:         write(*,*)'READING PROBE SEQUENCES'
24:         open(4,file= 'pseq8.dat',form=  'formatted',status='old')
25:         do 400 i=1,4
26:         do 400 j=1,259
27:             read(4,401)(pseq8(i,j,k),k=1,8)
28: 400         continue
29: 401         format(8a1)
30:             close(4)
31: c
32:         do 170 j=1,259
33:           do 170 k=1,8
34:             if(pseq8(1,j,k).eq.'a') then
35:                 pnum8(1,j,k)=1
36:             else
37:                 pnum8(1,j,k)=-1
38:             endif
39: 170         continue
40:         do 171 j=1,259
41:           do 171 k=1,8
42:             if(pseq8(2,j,k).eq.'c') then
43:                 pnum8(2,j,k)=2
44:             else
45:                 pnum8(2,j,k)=-2
46:             endif
47: 171         continue
48:         do 172 j=1,259
49:           do 172 k=1,8
50:             if(pseq8(3,j,k).eq.'g') then
51:                 pnum8(3,j,k)=3
```

```
52:              else
53:                 pnum8(3,j,k)=-3
54:              endif
55: 172       continue
56:        do 173 j=1,259
57:           do 173 k=1,8
58:              if(pseq8(4,j,k).eq.'t') then
59:                 pnum8(4,j,k)=4
60:              else
61:                 pnum8(4,j,k)=-4
62:              endif
63: 173       continue
64:        pnum8(1,1,8)=2
65:        pnum8(1,2,8)=3
66:        pnum8(1,3,8)=4
67:        pnum8(1,137,1)=2
68:        pnum8(1,138,1)=3
69:        pnum8(1,139,1)=4
70:        pnum8(2,1,8)=1
71:        pnum8(2,2,8)=3
72:        pnum8(2,3,8)=4
73:        pnum8(2,137,1)=1
74:        pnum8(2,138,1)=3
75:        pnum8(2,139,1)=4
76:        pnum8(3,1,8)=1
77:        pnum8(3,2,8)=2
78:        pnum8(3,3,8)=4
79:        pnum8(3,137,1)=1
80:        pnum8(3,138,1)=2
81:        pnum8(3,139,1)=4
82:        pnum8(4,1,8)=1
83:        pnum8(4,2,8)=2
84:        pnum8(4,3,8)=3
85:        pnum8(4,137,1)=1
86:        pnum8(4,138,1)=2
87:        pnum8(4,139,1)=3
88: c
89: c
90:        write(*,*)'ENTER PROBE DATA FILENAME:   A10'
91:        write(*,*)
92:        read(*,402)pdata
93: 402    format(a10)
94:        open(1,file=pdata     ,form='formatted',status='old')
95:        do 500 k=1,259
96:           read(1,501) na(k),nc(k),ng(k),nt(k)
97: 500    continue
98: 501    format(4i2)
99:        close(1)
100: c
101: c
102:       npxx=0
103:       npx=0
104:       np0=0
105:       do 600 i=1,259
106:          if(i.le.130) then
107:             if(na(i).ne.0) then
108:                do 602 k=1,na(i)
```

```
109:                   npx=npx+1
110:                   if(i.gt.3 .and. pseq8(1,i,8).ne.'0')npxx=npxx+1
111:                   pset(npx,1)=i
112: 602               pset(npx,2)=1
113:               endif
114: c
115:               if(nc(i).ne.0) then
116:                  do 604 k=1,nc(i)
117:                  npx=npx+1
118:                  if(i.gt.3 .and. pseq8(2,i,8).ne.'0')npxx=npxx+1
119:                  pset(npx,1)=i
120: 604              pset(npx,2)=2
121:               endif
122: c
123:               if(ng(i).ne.0) then
124:                  do 606 k=1,ng(i)
125:                  npx=npx+1
126:                  if(i.gt.3 .and. pseq8(3,i,8).ne.'0')npxx=npxx+1
127:                  pset(npx,1)=i
128: 606              pset(npx,2)=3
129:               endif
130: c
131:               if(nt(i).ne.0) then
132:                  do 608 k=1,nt(i)
133:                     npx=npx+1
134:                     if(i.gt.3 .and. pseq8(4,i,8).ne.'0')npxx=npxx+1
135:                     pset(npx,1)=i
136: 608                 pset(npx,2)=4
137:               endif
138: c
139:           else
140: c
141:               if(pseq8(1,i,8).ne.'0') then
142:                  if(na(i).ne.0) then
143:                     do 610 k=1,na(i)
144:                        np0=np0+1
145:                        npx=npx+1
146:                        pset(npx,1)=i
147: 610                    pset(npx,2)=1
148:                  endif
149: c
150:                  if(nc(i).ne.0) then
151:                     do 612 k=1,nc(i)
152:                        np0=np0+1
153:                        npx=npx+1
154:                        pset(npx,1)=i
155: 612                    pset(npx,2)=2
156:                  endif
157: c
158:                  if(ng(i).ne.0) then
159:                     do 614 k=1,ng(i)
160:                        np0=np0+1
161:                        npx=npx+1
162:                        pset(npx,1)=i
163: 614                    pset(npx,2)=3
164:                  endif
165: c
```

```
166:               if(nt(i).ne.0) then
167:                  do 616 k=1,nt(i)
168:                     np0=np0+1
169:                     npx=npx+1
170:                     pset(npx,1)=i
171: 616                 pset(npx,2)=4
172:               endif
173:             endif
174:           endif
175: 600   continue
176:         write(*,621)npx,np0,npxx
177: 621     format(1x,'npx=',i3,3x,'np0=',i3,2x,'npxx=',i3)
178: c
179: c
180:         write(*,*)'READING REGISTER TRANSITION TABLE'
181: c
182: c
183: c         The register transition table, TAB, is a logical
184: c         truth table for determining whether probe entries
185: c         and register entries properly overlap:  0 => no,
186: c         and 1 => yes.
187: c
188: c         notT  notG  notC  notA  -   A   C   G   T
189: c
190: c         (-4)  (-3)  (-2)  (-1) (0) (1) (2) (3) (4)
191: c
192: c    A (1)   1     1     1     0   -   1   0   0   0
193: c
194: c    C (2)   1     1     0     1   -   0   1   0   0
195: c
196: c    G (3)   1     0     1     1   -   0   0   1   0
197: c
198: c    T (4)   0     1     1     1   -   0   0   0   1
199: c
200: c
201:         open(1,file='tab.dat',form='formatted',status='old')
202:         do 800 i=1,4
203:            do 800 j=-4,4,1
204:               read(1,802)n
205:               tab(i,j)=n
206: 800   continue
207: 802     format(i1)
208:         close(1)
209: c
210: c
211:         write(*,*)'ENTER LEFT REGISTER VALUES'
212:         write(*,*)
213:         read(*,901)(lreg1(1,i),i=1,7)
214:         write(*,*)'ENTER RIGHT REGISTER VALUES'
215:         write(*,*)
216:         read(*,901)(rreg1(1,i),i=1,7)
217: 901     format(7i1)
218: c
219: c
220:         numreg=1
221: c
222: c
```

```
223:  c                  NUMREG is the current number of rregisters
224:  c
225:  c
226:          halt=int((npxx + (npx-npxx)/2)/2)
227:          write(*,622)halt
228:  622     format(1x,'Halt at ii=',i3)
229:          r1(1,1)=0
230:          l1(1,1)=0
231:          dr1num(1)=0
232:          dl1num(1)=0
233:          ii=0
234:  1000    ii=ii+1
235:  c
236:  c
237:  c                  ii indexes the round of comparisons.  ii is also
238:  c                  equal to the current length of candidate sequences.
239:  c
240:  c
241:          w=0
242:  c
243:  c
244:          do 1100 f=1,numreg
245:             do 1200 kk=1,npx-np0
246:                if(ii.eq.1) then
247:                   if(kk.gt.1 .and. pset(kk,1).eq.pset(r2(w,ii),1)
248:       1               .and. pset(kk,2).eq.pset(r2(w,ii),2) .and.
249:       2               skipa.eq.1) goto 1200
250:                   skipa=0
251:                   do 1550 j=1,7
252:  1550                if(tab(rreg1(f,j),pnum8(pset(kk,2),pset(kk,1),
253:       1                  j+1)).eq.0) goto 1200
254:                else
255:  c
256:                   do 1300 mm=1,ii-1
257:  1300                if(kk.eq.r1(f,mm) .or. kk.eq.l1(f,mm)) goto 1200
258:                   do 1400 mm=1,dl1num(f)
259:  1400                if(kk.eq.dl1(f,mm)) goto 1200
260:                   if(kk.gt.1 .and. pset(kk,1).eq.pset(r2(w,ii),1)
261:       1               .and. pset(kk,2).eq.pset(r2(w,ii),2) .and.
262:       2               skipa.eq.1) goto 1200
263:                   skipa=0
264:                   do 1500 j=1,7
265:  1500                if(tab(rreg1(f,j),pnum8(pset(kk,2),pset(kk,1),
266:       1                  j+1)).eq.0) goto 1200
267:                endif
268:  c
269:  c
270:                skipb=0
271:                if(pnum8(pset(kk,2),pset(kk,1),8).lt.0 .or.
272:       1           pset(kk,1).le.3) then
273:                   do 1600 jj=npx-np0+1,npx
274:                      if(ii.eq.1) then
275:                         if(jj.gt.1 .and. pset(jj,1).eq.pset(dr2(w,dr2num(w)),
276:       1                     1) .and. pset(jj,2).eq.pset(dr2(w,dr2num(w)),2)
277:       2                     .and. skipb.eq.1) goto 1600
278:                         skipb=0
```

```
279:                  do 1950 x=1,8
280:                     if(x.eq.1) then
281:                        if(tab(pset(kk,2),pnum8(pset(jj,2),pset(jj,1),
282:     1                      1)).eq.0) goto 1600
283:                     else
284:                        if(tab(rreg1(f,x-1),pnum8(pset(jj,2),
285:     1                      pset(jj,1),x)).eq.0) goto 1600
286:                     endif
287: 1950             continue
288:               else
289:                  do 1700 mm=1,dr1num(f)
290: 1700                if(jj.eq.dr1(f,mm)) goto 1600
291:                  do 1800 mm=1,ii-1
292: 1800                if(jj.eq.l1(f,mm)) goto 1600
293:                  if(jj.gt.1 .and. pset(jj,1).eq.pset(dr2(w,dr2num(w)),
294:     1                1) .and. pset(jj,2).eq.pset(dr2(w,dr2num(w)),2)
295:     2                .and. skipb.eq.1) goto 1600
296:                  skipb=0
297:                  do 1900 x=1,8
298:                     if(x.eq.1) then
299:                        if(tab(pset(kk,2),pnum8(pset(jj,2),pset(jj,1),
300:     1                      1)).eq.0) goto 1600
301:                     else
302:                        if(tab(rreg1(f,x-1),pnum8(pset(jj,2),
303:     1                      pset(jj,1),x)).eq.0) goto 1600
304:                     endif
305: 1900             continue
306:               endif
307:               ksave=kk
308:               jsave=jj
309:               w0=w
310: c
311:               call left(ii,w,f,jsave,ksave)
312: c
313:               if(w.eq.w0) goto 1600
314:               do 2000 k=w0+1,w
315:                  do 2100 i=1,6
316: 2100                rreg2(k,i+1)=rreg1(f,i)
317:                  rreg2(k,1)=pset(kk,2)
318:                  do 2600 q=1,dr1num(f)
319: 2600                dr2(k,q)=dr1(f,q)
320:                  dr2num(k)=dr1num(f) + 1
321:                  dr2(k,dr2num(k))=jj
322: 2000             continue
323:               if(ii.eq.1) then
324:                  do 2200 k=w0+1,w
325: 2200                r2(k,1)=kk
326:               else
327:                  do 2300 k=w0+1,w
328:                     do 2400 x=1,ii-1
329: 2400                   r2(k,x)=r1(f,x)
330: 2300                r2(k,ii)=kk
331:               endif
332:               skipa=1
333:               skipb=1
334: 1600       continue
335: c
```

```
336:              else
337: c
338:                  jsave=0
339:                  ksave=kk
340:                  w0=w
341: c
342:                  call left(ii,w,f,jsave,ksave)
343: c
344:                  if(w.eq.w0) goto 1200
345:                  do 2700 k=w0+1,w
346:                      do 2800i=1,6
347: 2800                     rreg2(k,i+1)=rreg1(f,i)
348:                          rreg2(k,1)=pset(kk,2)
349:                      do 2900 q=1,dr1num(f)
350: 2900                     dr2(k,q)=dr1(f,q)
351:                      dr2num(k)=dr2num(f)
352: 2700                 continue
353:                  if(ii.eq.1) then
354:                      do 6000 k=w0+1,w
355: 6000                     r2(k,1)=kk
356:                  else
357:                      do 6100 k=w0+1,w
358:                          do 6200 x=1,ii-1
359: 6200                         r2(k,x)=r1(f,x)
360: 6100                     r2(k,ii)=kk
361:                  endif
362:                  skipa=1
363:              endif
364: 1200     continue
365: 1100  continue
366: c
367: c
368:          write(*,*)
369:          numreg=w
370:          write(*,1101)ii,numreg
371: 1101     format(1x,'ii=',i4,3x,'numreg=',i5)
372:          do 7000 k=1,numreg
373:              do 7100 m=1,ii
374:                  r1(k,m)=r2(k,m)
375: 7100             l1(k,m)=l2(k,m)
376:              do 7200 m=1,7
377:                  rreg1(k,m)=rreg2(k,m)
378: 7200             lreg1(k,m)=lreg2(k,m)
379:              do 7300 m=1,dr2num(k)
380: 7300             dr1(k,m)=dr2(k,m)
381:              do 7400 m=1,dl2num(k)
382: 7400             dl1(k,m)=dl2(k,m)
383:              dr1num(k)=dr2num(k)
384:              dl1num(k)=dl2num(k)
385: 7000     continue
386:          if (ii.lt.halt) goto 1000
387: c
388: c
389: c            PRINT SEQUENCES
390: c
391: c
392:      do 3000 k=1,numreg
```

```
393:              write(*,*)
394:              write(*,3007)k
395:    3007      format(1x,'f=',i3)
396:              do 3200 m=1,halt
397:                 if(pset(l1(k,m),2) .eq. 1) seql(m)='A'
398:                 if(pset(l1(k,m),2) .eq. 2) seql(m)='C'
399:                 if(pset(l1(k,m),2) .eq. 3) seql(m)='G'
400:                 if(pset(l1(k,m),2) .eq. 4) seql(m)='T'
401:    3200      continue
402:              do 3100 m=halt,1,-1
403:                 if(pset(r1(k,m),2) .eq. 1) seqr(halt-m+1)='A'
404:                 if(pset(r1(k,m),2) .eq. 2) seqr(halt-m+1)='C'
405:                 if(pset(r1(k,m),2) .eq. 3) seqr(halt-m+1)='G'
406:                 if(pset(r1(k,m),2) .eq. 4) seqr(halt-m+1)='T'
407:    3100      continue
408:              write(*,*)
409:              write(*,4001)(seql(j),j=1,halt)
410:              write(*,4001)(seqr(j),j=1,halt)
411:    4001      format('0',40(1x,a1))
412:    3000    continue
413:    5000  end
414: c
415: c
416:          subroutine left(ii,w,f,jsave,ksave)
417:          implicit integer*2 (a-z)
418:          dimension r1(9999,120),r2(9999,120),l1(9999,120),l2(9999,120)
419:          dimension dr2(9999,120),dl1(9999,120),dl2(9999,120),dr1num(9999)
420:          dimension dr2num(9999),dl1num(9999),dl2num(9999),pset(240,2)
421:          dimension pnum8(4,259,8),rreg1(9999,7),rreg2(9999,7)
422:          dimension lreg2(9999,7),lreg1(9999,7)
423:          dimension tab(4,-4:4),dr1(9999,120)
424:          character*1 pseq8(4,259,8)
425:          common r1,r2,l1,l2,dr1,dr2,dl1,dl2,rreg1,rreg2,lreg1,lreg2,
426:         1       pnum8,tab,dr1num,dr2num,dl1num,dl2num,npx,np0,pset,pseq8
427: c
428: c
429:          skipa=0
430:          do 1000 hh=1,npx
431:             if(pnum8(pset(hh,2),pset(hh,1),8).lt.0 .or.
432:         1      pset(hh,1).le.3 .or. hh.eq.jsave) goto 1000
433:             if(ii.eq.1) then
434:                if(hh.gt.1 .and. pset(hh,1).eq.pset(l2(w,ii),1)
435:         1         .and. pset(hh,2).eq.pset(l2(w,ii),2) .and.
436:         2         skipa.eq.1) goto 1000
437:                skipa=0
438:                do 1350 j=1,7
439:    1350           if(tab(lreg1(f,j),pnum8(pset(hh,2),pset(hh,1),j))
440:         1            .eq.0) goto 1000
441:             else
442: c
443:                do 1100 mm=1,ii-1
444:    1100           if(hh.eq.r1(f,mm) .or. hh.eq.l1(f,mm)) goto 1000
445:                do 1200 mm=1,dr1num(f)
446:    1200           if(hh.eq.dr1(f,mm)) goto 1000
447:                if(hh.gt.1 .and. pset(hh,1).eq.pset(l2(w,ii),1)
448:         1         .and. pset(hh,2).eq.pset(l2(w,ii),2) .and.
449:         2         skipa.eq.1) goto 1000
```

```
450:                    skipa=0
451:                    do 1300 j=1,7
452: 1300                  if(tab(lreg1(f,j),pnum8(pset(hh,2),pset(hh,1),j))
453:        1                 .eq.0) goto 1000
454:                    endif
455: c
456: c
457:                    skipb=0
458:                    if(pset(hh,1).ge.137) then
459:                       do 1400 rr=1,npx-np0
460:                       if(rr.eq.ksave) goto 1400
461:                       if(ii.eq.1) then
462:                          if(rr.gt.1 .and. pset(rr,1).eq.pset(dl2(w,dl2num(w)),
463:        1                    1) .and. pset(rr,2).eq.pset(dl2(w,dl2num(w)),2)
464:        2                    .and. skipb.eq.1) goto 1400
465:                          skipb=0
466:                          do 1750 x=1,8
467:                             if(x.eq.8) then
468:                                if(tab(pnum8(pset(hh,2),pset(hh,1),x),
469:        1                          pnum8(pset(rr,2),pset(rr,1),x)).eq.0)
470:        2                          goto 1400
471:                             else
472:                                if(tab(lreg1(f,x),pnum8(pset(rr,2),pset(rr,1),
473:        1                          x)).eq.0) goto 1400
474:                             endif
475: 1750                     continue
476:                       else
477: c
478:                          do 1500 mm=1,dl1num(f)
479: 1500                        if(rr.eq.dl1(f,mm)) goto 1400
480:                          do 1600 mm=1,ii-1
481: 1600                        if(rr.eq.r1(f,mm)) goto 1400
482:                          if(rr.gt.1 .and. pset(rr,1).eq.pset(dl2(w,dl2num(w)),
483:        1                    1) .and. pset(rr,2).eq.pset(dl2(w,dl2num(w)),2)
484:        2                    .and. skipb.eq.1) goto 1400
485:                          skipb=0
486:                          do 1700 x=1,8
487:                             if(x.eq.8) then
488:                                if(tab(pnum8(pset(hh,2),pset(hh,1),x),
489:        1                          pnum8(pset(rr,2),pset(rr,1),x)).eq.0)
490:        2                          goto 1400
491:                             else
492:                                if(tab(lreg1(f,x),pnum8(pset(rr,2),pset(rr,1),
493:        1                          x)).eq.0) goto 1400
494:                             endif
495: 1700                     continue
496:                       endif
497:                       skipa=1
498:                       skipb=1
499:                       w=w+1
500:                       dl2num(w)=dl1num(f)+1
501:                       do 1710 k=1,dl1num(f)
502: 1710                     dl2(w,k)=dl1(f,k)
503:                       dl2(w,dl2num(w))=rr
504: c
505:                       do 1800 i=1,6
506: 1800                     lreg2(w,i)=lreg1(f,i+1)
```

```
507:                lreg2(w,7)=pset(hh,2)
508:             if(ii.eq.1) then
509:                12(w,1)=hh
510:             else
511:                do 1900 k=1,ii-1
512: 1900              12(w,k)=11(f,k)
513:                   12(w,ii)=hh
514:             endif
515: 1400     continue
516:       else
517:          skipa=1
518:          w=w+1
519:          dl2num(w)=dl1num(f)
520:          do 2200 j=1,dl1num(f)
521: 2200        dl2(w,j)=dl1(f,j)
522:          do 2000 i=1,6
523: 2000        lreg2(w,i)=lreg1(f,i+1)
524:             lreg2(w,7)=pset(hh,2)
525:          if(ii.eq.1) then
526:             12(w,1)=hh
527:          else
528:             do 2100 k=1,ii-1
529: 2100           12(w,k)=11(f,k)
530:                12(w,ii)=hh
531:          endif
532:       endif
533: 1000  continue
534:       return
535:       end
```

I claim:

1. A method for determining the nucleotide sequence of a nucleic acid, the method comprising the steps of:
   providing a set of probes, each probe within the set having a predetermined length and each probe within the set having a predetermined sequence of fixed and non-fixed positions, the fixed positions comprising one or more predetermined kinds of nucleotides;
   hybridizing the probes of the set to the nucleic acid;
   determining the number of copies of each probe in the set that form perfectly matched duplexes with the nucleic acid; and
   reconstructing the nucleotide sequence of the nucleic acid from the predetermined sequences of the probes that form perfectly matched duplexes with the nucleic acid.

2. The method of claim 1 wherein said set contains at least one probe comprising a sequence of fixed and nonfixed positions equivalent to that of each permutation of a plurality of fixed and non-fixed positions equal to or less than the length of the probe.

3. The method of claim 2 wherein said step of hybridizing includes:
   anchoring a known quantity of said nucleic acid to each of a plurality of solid phase supports; and
   washing each of the solid phase supports so that said probes forming perfectly matched duplexes with said nucleic acid are detectable.

4. The method of claim 3 wherein said step of hybridizing includes separately hybridizing each probe of said set to said nucleic acid on a different solid phase support of said plurality of solid phase supports.

5. The method of claim 4 wherein said predetermined length of said probes are in the range of from seven to eleven nucleotides, inclusive.

6. The method of claim 5 wherein said non-fixed positions of said probes are occupied by at least one degeneracy-reducing analog.

7. The method of claim 6 wherein said degeneracy-reducing analog is deoxyinosine whenever said fixed positions are occupied by nucleotides containing either cytosine or adenosine.

8. The method of claim 6 wherein said degeneracy-reducing analog is 2-aminopurine whenever said fixed positions are occupied by nucleotides containing either cytosine or guanosine.

9. The method of claim 6 wherein said degeneracy-reducing analog is $N^4$-methoxydeoxycytidine or 5-fluorodeoxyuridine whenever said fixed positions are occupied by nucleotides containing either adenosine or guanosine.

10. The method of claim 6 wherein said degeneracy-reducing analog minimizes the differences in binding energy between basepairs.

11. A kit for determining the nucleotide sequence of a nucleic acid, the kit comprising a set of oligonucleotides, each oligonucleotide within the set having a predetermined length and each oligonucleotide within the set having a predetermined sequence of fixed and non-fixed positions, the fixed positions comprising one or more predetermined kinds of nucleotides, and the set containing at least one probe comprising a sequence of fixed and non-fixed positions equivalent to that of each permutation of a plurality of fixed and non-fixed positions less than or equal to the length of the probe.

12. The kit of claim 11 further including a labelling means for detecting oligonucleotides capable of forming perfectly matched duplexes with said nucleic acid.

13. The kit of claim 12 further including a plurality of solid phase supports for anchoring said nucleic acid.

14. The kit of claim 13 further including a prehybridization solution for treating said solid phase supports to minimize nonspecific binding of said oligonucleotides to said solid phase supports.

15. The kit of claim 14 further including a set of maximally non-complementary oligonucleotides for each oligonucleotide of said set, the maximally non-complementary oligonucleotides being used with said prehybridization solution to block nonspecific binding sites of said oligonucleotides.

16. The kit of claim 12 wherein said labelling means includes a radioactive isotope covalently attached to said oligonucleotides.

17. The kit of claim 12 wherein said labelling means includes a fluorescent dye or an enzyme capable of generating a colorimetric signal.

18. The kit of claim 17 wherein said labelling means includes biotin conjugated to said oligonucleotides and includes avidin or streptavidin conjugated to said fluorescent dye or said enzyme capable of generating a colorimetric signal.

19. A method for determining the nucleotide sequence of a nucleic acid, the method comprising the steps of:

providing a first set of probes, each probe within the first set having the same length, the length being from seven to ten nucleotides, and each probe within the first set having a predetermined sequence of fixed and non-fixed bases, the fixed bases being deoxyadenosine and the non-fixed bases comprising deoxycytosine, deoxyguanosine, thymidine, or a degeneracy-reducing analog thereof, such that for each permutation of fixed and non-fixed bases less than or equal to the length of the probe, the first set contains at least one probe having a sequence equivalent to such permutation;

providing a second set of probes, each probe within the second set having the same length, the length being from seven to ten nucleotides, and each probe within the second set having a predetermined sequence of fixed and non-fixed bases, the fixed bases being deoxycytosine and the non-fixed bases comprising deoxyadenosine, deoxyguanosine, thymidine, or a degeneracy-reducing analog thereof, such that for each permutation of fixed and non-fixed bases less than or equal to the length of the probe, the second set contains at least one probe having a sequence equivalent to such permutation;

providing a third set of probes, each probe within the third set having the same length, the length being from seven to ten nucleotides, and each probe within the third set having a predetermined sequence of fixed and non-fixed bases, the fixed bases being deoxyguanosine and the non-fixed bases comprising deoxyadenosine, deoxycytosine, thymidine, or a degeneracy-reducing analog thereof, such that for each permutation of fixed and non-fixed bases less than or equal to the length of the probe, the third set contains at least one probe having a sequence equivalent to such permutation;

providing a fourth set of probes, each probe within the fourth set having the same length, the length being from seven to ten nucleotides, and each probe within the fourth set having a predetermined sequence of fixed and non-fixed bases, the fixed bases being thymidine and the non-fixed bases comprising deoxyadenosine, deoxycytosine, deoxyguanosine, or a degeneracy-reducing analog thereof, such that for each permutation of fixed and non-fixed bases the length of the probe, the fourth set contains at least one probe having a sequence equivalent to such permutation;

anchoring a known quantity of the nucleic acid to each of a plurality of solid phase supports;

separately hybridizing each probe of the first, second, third, and fourth sets to the nucleic acid anchored on the solid phase supports;

washing each of the solid phase supports after hybridizing said probes so that said probes forming perfectly matched duplexes with said nucleic acid are detectable;

determining the number of copies of each probe in each set that form perfectly matched duplexes with the nucleic acid; and reconstructing the nucleotide sequence of the nucleic acid from the predetermined sequences of the probes that form perfectly matched duplexes with the nucleic acid.

20. The method of claim 19 wherein said nucleic acid contains at least one known sequence region.

21. The method of claim 20 wherein said probe of said first set having said length from eight to nine nucleotides, said probe of said second set having said length from eight to nine nucleotides, said probe of said third set having said length from eight to none nucleotides, and said probe of said fourth set having said length from eight to nine nucleotides.

22. The method of claim 21 wherein the said degeneracy-reducing analog of said first set includes deoxyinosine, 5-fluorodeoxyuridine, and $N^4$-methoxycytosine, said degeneracy-reducing analog of said second set includes deoxyinosine and 2-aminopurine, and said degeneracy-reducing analog of said third set includes 2-aminopurine and $N^4$-methoxycytosine.

23. The method of claim 22 wherein said step of washing includes exposing each one of said plurality of solid phase supports to tetramethylammonium chloride at a concentration of between about 2 to 4 moles per liter.

* * * * *